United States Patent
Diab et al.

(10) Patent No.: US 6,643,530 B2
(45) Date of Patent: Nov. 4, 2003

(54) METHOD AND APPARATUS FOR DEMODULATING SIGNALS IN A PULSE OXIMETRY SYSTEM

(75) Inventors: Mohamed K. Diab, Mission Viejo, CA (US); Walter M. Weber, Laguna Hills, CA (US); Ammar Al-Ali, Costa Mesa, CA (US)

(73) Assignee: Masimo Corporation, Irvine, CA (US)

( * ) Notice: Subject to any disclaimer, the term of this patent is extended or adjusted under 35 U.S.C. 154(b) by 50 days.

(21) Appl. No.: 09/735,960

(22) Filed: Dec. 13, 2000

(65) Prior Publication Data

US 2001/0002206 A1 May 31, 2001

Related U.S. Application Data

(62) Division of application No. 09/058,799, filed on Apr. 10, 1998.
(60) Provisional application No. 60/043,620, filed on Apr. 14, 1997.

(51) Int. Cl.$^7$ .................................................. A61B 5/00
(52) U.S. Cl. ....................................... 600/323; 600/336
(58) Field of Search ................................... 600/310, 322, 600/323, 330, 336; 356/39, 41, 323; 250/339.01, 339.06

(56) References Cited

U.S. PATENT DOCUMENTS

| | | |
|---|---|---|
| 3,638,640 A | 2/1972 | Shaw |
| 3,704,706 A | 12/1972 | Herczfeld et al. |
| 4,407,290 A | 10/1983 | Wilber |
| 4,773,422 A | 9/1988 | Isaacson et al. |
| 4,785,463 A | 11/1988 | Janc et al. |

(List continued on next page.)

FOREIGN PATENT DOCUMENTS

| | | |
|---|---|---|
| DE | 3328862 A1 | 2/1985 |
| EP | 0 335 357 | 3/1989 |
| EP | 0 761 159 A2 | 6/1996 |
| WO | WO 94/09698 | 9/1993 |
| WO | WO 98/46125 | 4/1998 |

*Primary Examiner*—Eric F. Winakur
(74) *Attorney, Agent, or Firm*—Knobbe, Martens, Olson & Bear LLP

(57) ABSTRACT

A method and an apparatus measure blood oxygenation in a subject. A first signal source applies a first input signal during a first time interval. A second signal source applies a second input signal during a second time interval. A detector detects a first parametric signal responsive to the first input signal passing through a portion of the subject having blood therein. The detector also detects a second parametric signal responsive to the second input signal passing through the portion of the subject. The detector generates a detector output signal responsive to the first and second parametric signals. A signal processor receives the detector output signal and demodulates the detector output signal by applying a first demodulation signal to a signal responsive to the detector output signal to generate a first output signal responsive to the first parametric signal. The signal processor applies a second demodulation signal to the signal responsive to the detector output signal to generate a second output signal responsive to the second parametric signal. The first demodulation signal and the second demodulation signal both include at least a first component having a first frequency and a first amplitude and a second component having a second frequency and a second amplitude. The second frequency is a harmonic of the first frequency. The second amplitude is related to the first amplitude to minimize crosstalk from the first parametric signal to the second output signal and to minimize crosstalk from the second parametric signal to the first output signal.

9 Claims, 18 Drawing Sheets

U.S. PATENT DOCUMENTS

| | | |
|---|---|---|
| 4,824,242 A | 4/1989 | Frick et al. |
| 4,848,901 A | 7/1989 | Hood, Jr. |
| 4,863,265 A | 9/1989 | Flower et al. |
| 4,867,571 A | 9/1989 | Frick et al. |
| 4,948,248 A | 8/1990 | Lehman |
| 5,276,705 A | 1/1994 | Higgins |
| 5,349,952 A | 9/1994 | McCarthy et al. |
| RE35,122 E | 12/1995 | Corenman et al. |
| 5,521,938 A | 5/1996 | Stewart et al. |
| 5,555,882 A | 9/1996 | Richardson et al. |
| 5,579,341 A | 11/1996 | Smith et al. |
| 5,640,416 A | 6/1997 | Chalmers |
| 5,919,134 A * | 7/1999 | Diab .......................... 600/323 |
| 5,940,346 A | 8/1999 | Sadowsky et al. |

* cited by examiner

METHOD AND APPARATUS FOR DEMODULATING SIGNALS IN A PULSE OXIMETRY SYSTEM

REFERENCE TO RELATED APPLICATION

The present application is a divisional of application Ser. No. 09/058,799 filed on Apr. 10, 1998, the contents of which is expressly incorporated by reference in its entirety. Also claims benefit to U.S. Provisional Application No. 60/043,620 filed Apr. 14, 1997.

BACKGROUND OF THE INVENTION

1. Field of the Invention

The present invention relates to the field of signal processing, and, more particularly, relates to the field of processing of signals generated in a physiological monitoring system, such as, for example, in a system for measuring blood oxygen saturation using pulse oximetry.

2. Description of the Related Art

The present invention will be described herein in connection with a pulse oximetry apparatus and a method, which are used to measure blood oxygen saturation in a subject, such as, for example, a human patient. The teachings of the present invention can be used in other applications wherein useable signal information is obtained in a noisy environment.

In an exemplary pulse oximetry apparatus and a corresponding method, blood oxygen saturation is determined by transmitting pulses of electromagnetic energy through a portion of a subject which has blood flowing therein (e.g., through a finger, through an ear lobe, or other portion of the body where blood flows close to the skin). In the examples described herein, the pulses of electromagnetic energy comprise periodic pulses of red light having wavelengths of approximately 660 nanometers, for example, and periodic pulses of infrared light having wavelengths of approximately 905 nanometers. As described, for example, in U.S. Pat. No. 5,482,036 and in U.S. Pat. No. 5,490,505, the pulses of red light and the pulses of infrared light are applied with the same periodicity but in an alternating and non-overlapping manner. In particular, in preferred embodiments, the red pulses are active for approximately 25% of each cycle and the infrared pulses are also active for approximately 25% of each cycle. The red pulses are separated in time from the infrared pulses such that both pulses are inactive for approximately 25% of each cycle between a red pulse and the next infrared pulse and both pulses are inactive for approximately 25% of each cycle between an infrared pulse and the next red pulse. (Although described herein below in connection with pulses having 25% duty cycles, it should be understood by persons of skill in the art that the duty cycles of the pulses can be changed in some applications.) After propagating through the portion of the subject, the red pulses and the infrared pulses are detected by a detector which is responsive to light at both wavelengths and which generates an electrical signal which has a predictable relationship to the intensity of the electromagnetic energy incident on the detector. The electrical signal is processed in accordance with the present invention to provide a representation of the blood oxygen saturation of the subject.

In conventional time division multiplexing (TDM) demodulation that uses rectangular waves to drive the red and infrared LEDs, the conventional process of demodulation using square waves can result in the aliasing of the ambient noise components that come close to the sidebands of harmonics and the fundamental frequency of the rectangular waves, and the noise components are thus collapsed into the output signal generated by the demodulation. In particular, it is very difficult to avoid including harmonics of the line frequency in the demodulated output signal.

SUMMARY OF THE INVENTION

The present invention avoids the problems associated with conventional demodulation and separation of TDM signals. In particular, the present invention avoids the problem of aliasing of the ambient noise into the passband of the system by selectively demodulating certain harmonics of the TDM signal. For example, in one embodiment, only two harmonics (e.g., the fundamental and the first harmonic) are demodulated. In other embodiments, more harmonics are demodulated. The present invention specifically addresses solutions to problems caused by crosstalk resulting from filtering and also resulting from demodulating with only certain harmonics instead of demodulating with all harmonics as is done using conventional square wave demodulation. In a digital implementation of the present invention, the output of the photodetector is initially sampled at a very high frequency (e.g., 46,875 Hz), and the signals are decimated (where decimation is lowpass filtering followed by sample rate compression) such that the final output signals are generated at a relatively low sampling rate (e.g., 62.5 Hz) which provides increased resolution at the output. Thus, bandwidth is traded for resolution in the output signal, thus increasing the signal to noise ratio.

One aspect of the present invention is an apparatus for measuring blood oxygenation in a subject. The apparatus comprises a first signal source which applies a first input signal during a first time interval. A second signal source applies a second input signal during a second time interval. A detector detects a first parametric signal responsive to the first input signal passing through a portion of the subject having blood therein. The detector also detects a second parametric signal responsive to the second input signal passing through the portion of the subject. The detector generates a detector output signal responsive to the first and second parametric signals. A signal processor receives the detector output signal. The signal processor demodulates the detector output signal by applying a first demodulation signal to a signal responsive to the detector output signal to generate a first output signal responsive to the first parametric signal and by applying a second demodulation signal to the signal responsive to the detector output signal to generate a second output signal responsive to the second parametric signal. Each of the first demodulation signal and the second demodulation signal comprises at least a first component having a first frequency and a first amplitude and a second component having a second frequency and a second amplitude. The second frequency is a harmonic of the first frequency. The second amplitude is selected to be related to the first amplitude to minimize crosstalk from the first parametric signal to the second output signal and to minimize crosstalk from the second parametric signal to the first output signal. In one embodiment, the second amplitude is determined by turning off one of the first and second signal sources and measuring the crosstalk between one of the parametric signals and the non-corresponding output signal while varying the second amplitude. A second amplitude is selected that minimizes the measured crosstalk.

Another aspect of the present invention is a method of minimizing crosstalk between two signals generated by applying a first pulse and a second pulse to measure a parameter. The first pulse and the second pulse are applied periodically at a first repetition rate defining a period. The first pulse is generated during a first interval in each period, and the second pulse is generated during a second interval in each period. The second interval is spaced apart from the first interval. The first and second pulses produce first and second parametric signals responsive to the parameter. The first and second parametric signals are received by a single detector that outputs a composite signal responsive to the first and second parametric signals. The method comprises the step of applying a first demodulation signal to the composite signal to generate a first demodulated output signal wherein the first demodulation signal comprises at least a first component having a first frequency corresponding to the first repetition rate. The first component has a first amplitude. The first demodulation signal further comprises a second component having a second frequency that is a harmonic of the first frequency. The second component has a second amplitude which has a selected proportional relationship to the first amplitude. The method further includes the step of applying a second demodulation signal to the composite signal to generate a second demodulated output signal. The second demodulation signal comprises the first component at the first frequency and the first amplitude and further comprises the second component at the second frequency and the second amplitude. At least one of the first and second components of the second demodulation signal has a selected phase difference with respect to the corresponding one of the first and second components of the first demodulation signal. The method further includes the steps of lowpass filtering the first demodulated output signal to generate a first recovered output signal responsive to the first parametric signal; and lowpass filtering the second demodulated output signal to generate a second recovered output signal responsive to the second parametric signal.

Preferably, the selected phase difference is $\pi$. Also preferably, the first pulse and the second pulse are generally rectangular pulses having a respective duty cycle. The rectangular pulses comprise a plurality of sinusoidal components including a fundamental component corresponding to the first frequency and a first harmonic component corresponding to the second frequency. The fundamental component has a fundamental component amplitude and the first harmonic component has a first harmonic component amplitude. The first harmonic component amplitude is related to the fundamental harmonic component amplitude by a first proportionality value. The second amplitude of the second component of the first demodulation signal is related to the first amplitude of the first component of the first demodulation signal by a second proportionality value which is approximately the inverse of the first proportionality value.

The method in accordance with this aspect of the invention preferably includes the further steps of sampling the composite signal when neither the first pulse nor the second pulse is active to obtain a sampled signal; and measuring the sampled signal to determine a noise level of the parametric signals.

In a further embodiment according to this aspect of the present invention, the method further includes the steps of performing a transform on the composite signal to generate a spectra of the composite signal; sampling the spectra at a plurality of frequencies other than at predetermined ranges of frequencies around the first frequency and around harmonics of the first frequency; determining an average of the magnitudes of the sampled plurality of frequencies; and comparing the average to a selected threshold to determine whether the average magnitude exceeds the selected threshold.

Another aspect of the present invention is a method of demodulating a composite signal generated by applying first and second periodic pulses of electromagnetic energy to a system having a parameter to be measured and by receiving signals responsive to the electromagnetic energy after having passed through the system and being affected by the parameter being measured. The signals are received as a composite signal having components responsive to the first and second pulses. The method comprises the step of applying a first demodulation signal to the composite signal to generate a first demodulated signal. The first demodulation signal comprises a first component having a first frequency corresponding to a repetition frequency of the first and second pulses and comprises a second component having a frequency that is a harmonic of the first frequency. The first component has a first amplitude and the second component has a second amplitude. The second amplitude has a predetermined relationship to the first amplitude. The predetermined relationship is selected to cause the first demodulated signal to have low frequency components responsive only to the first pulse. The method includes the further step of lowpass filtering the first demodulated signal to generate a first output signal. The first output signal varies in response to an effect of the parameter on the electromagnetic energy received from the first pulse.

Preferably, the method in accordance with this aspect of the invention includes the further step of applying a second demodulation signal to the composite signal to generate a second demodulated signal. The second demodulation signal has first and second components corresponding to the first and second components of the first demodulation signal. At least one of the first and second components of the second demodulation signal has a selected phase relationship with the corresponding one of the first and second components of the first demodulation signal. The method includes the further step of lowpass filtering the second demodulated signal to generate a second output signal. The second output signal varies in response to an effect of the parameter on the electromagnetic energy received from the second pulse.

Another aspect of the present invention is a pulse oximetry system that comprises a modulation signal generator. The modulation signal generator generates a first modulation signal that comprises a first pulse that repeats at a first repetition frequency. The first pulse has a duty cycle of less than 50%. The modulation signal generator generates a second modulation signal comprising a second pulse that also repeats at the first repetition frequency. The second pulse has a duty cycle of less than 50%. The second pulse occurs at non-overlapping times with respect to the first pulse. Each of the first and second pulses comprises a plurality of components wherein a first component has a frequency corresponding to the repetition frequency and wherein a second component has a second frequency corresponding to twice the first frequency. The second component has an amplitude which has a first predetermined relationship to an amplitude of the first component. A first transmitter emits electromagnetic energy at a first wavelength in response to the first pulse; and a second transmitter emits electromagnetic energy at a second wavelength in response to the second pulse. A detector receives electromagnetic energy at the first and second wavelengths after passing through a portion of a subject and generates a detector output signal responsive to the received electromagnetic energy. The detector output signal includes a signal component responsive to attenuation of the electromagnetic energy at the first wavelength and a signal component responsive to attenuation of the electromagnetic energy at the second wavelength. A first demodulator multiplies the detector signal by a first demodulation signal and generates a first demodulated output signal. The first demodulation signal comprises a first component having the first frequency and having a first amplitude. The first demodulation signal also comprises a second component having the second frequency and having a second amplitude. The second amplitude has a second predetermined relationship to the first amplitude. The second predetermined relationship is approximately inversely proportional to the first predetermined relationship. A second demodulator multiplies the detector signal by a second demodulation signal and generates a second demodulated output signal. The second demodulation signal comprises a first component having the first frequency and having the first amplitude. The second demodulation signal further comprises a second component having the second frequency and having the second amplitude. At least one component of the second demodulation signal has a selected phase relationship with a corresponding one component of the first demodulation signal. Preferably, the selected phase relationship is a $\pi$ phase difference.

Another embodiment incorporates decimation before demodulation. In yet another embodiment, a multi-channel demodulator, with or without pre-demodulation decimation is disclosed.

In yet another embodiment, an adaptive algorithm is used to control the operation of pre-demodulation decimators and post-demodulation decimators. The adaptive algorithm may control both the characteristics of a lowpass filter in the decimator and the decimation rate provided by a signal rate compressor in the decimator.

Another embodiment of the invention is a method for selecting a sample rate that reduces the interference caused by ambient light.

BRIEF DESCRIPTION OF THE DRAWINGS

The present invention will be described below in connection with the accompanying drawing figures in which.

DETAILED DESCRIPTION OF THE PREFERRED EMBODIMENT

Figure 1:
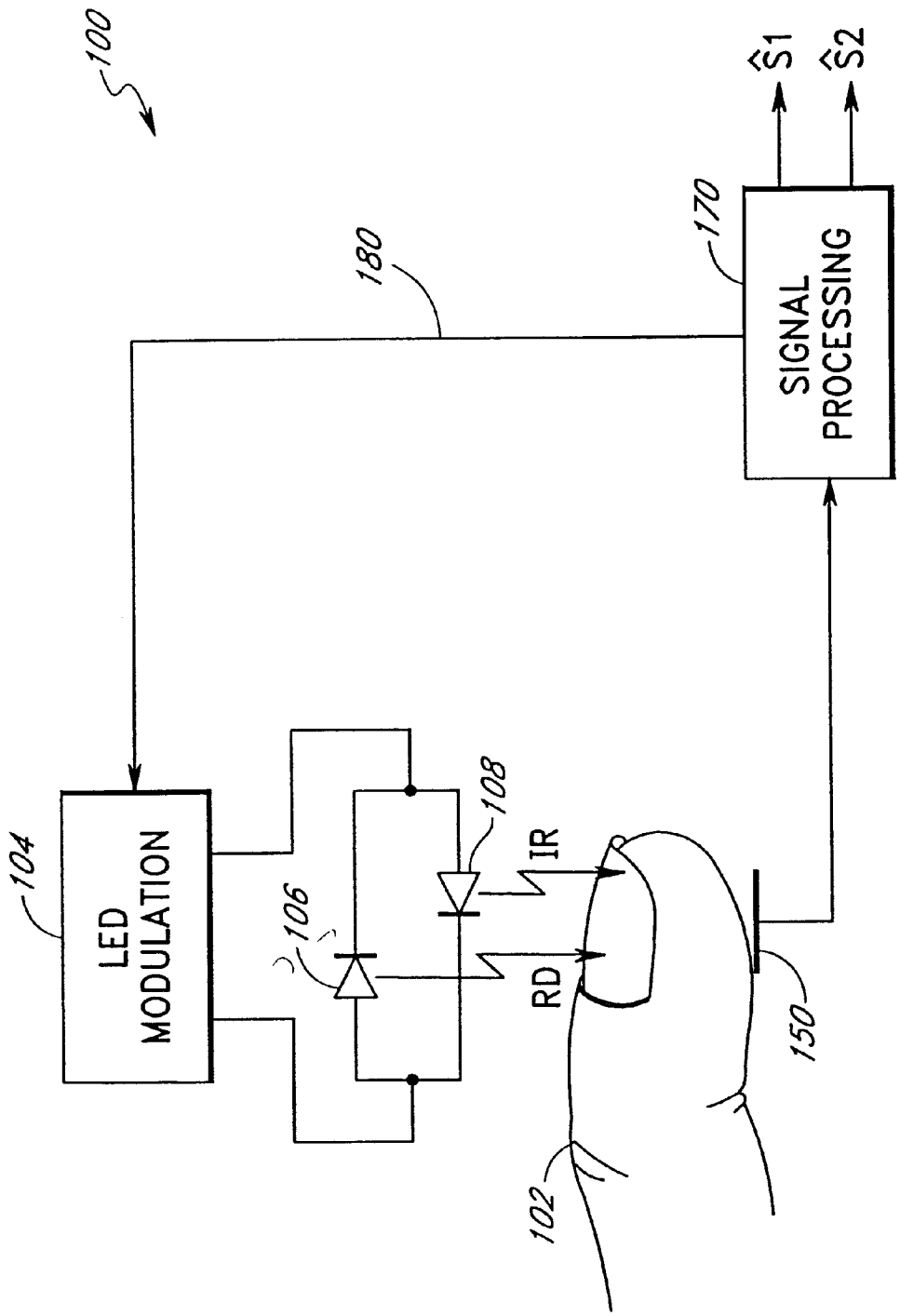
FIG. 1 illustrates an exemplary block diagram of a representation of a signal processing system in accordance with the present invention used to determine blood oxygen saturation in a subject.

FIG. 1 illustrates an exemplary block diagram of a representation of a signal processing system 100 in accordance with the present invention used to determine blood oxygen saturation in a subject, such as, for example, a human subject. In the example presented, the measurements are performed on a portion of the subject, such as a finger 102 illustrated in FIG. 1. An LED modulation circuit 104 drives a pair of back-to-back light emitting diodes (LEDs) 106, 108 by applying a periodic signal to the two light emitting diodes 106, 108. The LED 106 is selected to emit electromagnetic energy in the red visible light range, and has a wavelength of, for example, approximately 660 nanometers. The LED 108 is selected to emit electromagnetic energy in the infrared range, and has a wavelength of, for example, approximately 905 nanometers. The LED modulation circuit 104 supplies current in alternating directions so that the two LEDs 106, 108 are activated one at a time. In particular, as illustrated by a current waveform 120 in FIG. 2, current is first applied in a forward direction with respect to the red LED 106 during a first time interval 122 having a duration $\tau$. Thereafter, no current is applied to either LED during a second time interval 124 having a like duration $\tau$. Then, current is applied in a forward direction with respect to the infrared LED 108 during a third time interval 126, also having a duration $\tau$. Then, no current is applied to either LED during a fourth time interval 128 having a like duration $\tau$. Thereafter, the current is again applied in the forward direction for the red LED 106 during a fifth time interval 130 which corresponds to the first time interval 122. It can be seen that the overall cycle repeats with a period of duration T equal to 4τ. The red LED 106 emits light only when the current is applied in the forward direction with respect to the red LED 106. Thus, as illustrated by a red intensity waveform 132, the red LED 106 emits light as a pulse 134 during the first time interval 122 and as a pulse 136 during the fifth time interval 130, and so on. The red pulses repeat with a periodicity equal to T. Similarly, the infrared LED 108 emits infrared light only when the current is applied in the forward direction with respect to the infrared LED 108. Thus, as illustrated by an infrared intensity waveform 140, the infrared LED 108 emits infrared light as a pulse 142 during the third interval 126. A next infrared pulse 144 occurs at an interval T after the infrared pulse 142. Thus, the infrared pulses also repeat with a periodicity equal to T. It can be seen that the red pulses and the infrared pulses each have a duty cycle of 25%, and the red pulses and the infrared pulses are separated by intervals of one-fourth of each period T (i.e., the beginning of one pulse occurs an interval τ after the end of the previous pulse).

As further illustrated in FIG. 1, the electromagnetic energy pulses from the red LED 106 and the infrared LED 108 are applied to the finger 102. A detector 150 is positioned to receive the electromagnetic energy after the energy has passed through a portion of the finger 102. The detector 150 is selected to be responsive to both the red light and the infrared light and to generate an output signal responsive to the intensity of the energy received from each source. An exemplary current output signal from the detector 150 is represented by a waveform 152 in FIG. 2. As illustrated, the detector signal waveform 152 comprises a first pulse 154 responsive to the first red pulse 134, a second pulse 156 responsive to the infrared pulse 142 and a third pulse 158 responsive to the second red pulse 136. During the time between the first pulse 154 and the second pulse 156, the detector signal waveform 152 comprises noise 160, and during the time between the second pulse 156 and the third pulse 158, the detector signal waveform 150 comprises noise 162. The signal pulses 154, 156 and 158 also include noise superimposed thereon. Although shown as repeating noise, it should be understood that the noise varies with time. For example, noise caused by ambient light will vary with a periodicity corresponding to the 50 Hz or 60 Hz power frequency and their harmonics, particularly when the ambient light is provided by fluorescent lights which generate significant noise at the first harmonic (i.e., 100 Hz or 120 Hz) and the third harmonic (i.e., 200 Hz or 240 Hz).

The output of the detector 150 is applied as an input to a signal processor block 170 which processes the detector signal and generates a first signal $\hat{S}_1(t)$ responsive to the detected intensity of the red light incident on the detector 150 and generates a second signal $\hat{S}_2(t)$ responsive to the detected intensity of the infrared light incident on the detector 150. As illustrated, the signal processing block 170 is synchronized with the LED modulator 104 via a set of control lines 180. As will be discussed below, the control lines 180 advantageously communicate signals which provide timing information that determines when to activate the red LED 106 and when to activate the infrared LED 108.

Figure 3:
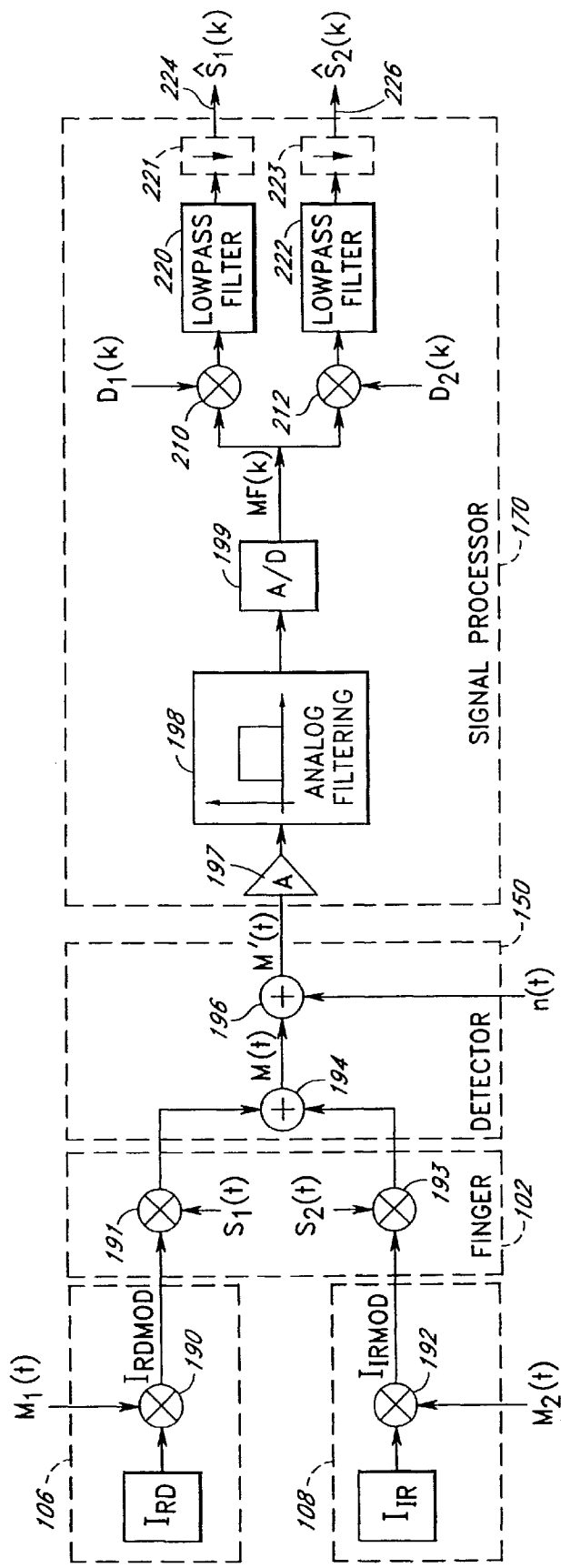
FIG. 3 illustrates a block diagram of the overall processing system in accordance with the present invention.

FIG. 3 is a pictorial representation of a model of an exemplary system which incorporates the present invention. The red LED 106 provides a light intensity represented as $I_{RD}$, and the infrared LED 108 provides a light intensity represented as $I_{IR}$. The effects of turning the LEDs 106, 108 on and off on periodic bases are modeled by a first multiplier or modulator 190 which applies a first modulation signal $M_1(t)$ to the red light intensity to generate a modulated red signal $I_{RDMOD}(t)$ and by a second multiplier or modulator 192 which applies a second modulation signal $M_2(t)$ to the infrared light intensity to generate a modulated infrared signal $I_{IRMOD}(t)$. The modulated light red signal and the modulated infrared signal are applied to the finger 102, or other body portion, as described above. The finger 102 has blood flowing therein and is represented in FIG. 3 as a block 102. The blood in the finger 102 has a volume and scattering components which vary throughout each cardiac cycle. The blood carries oxygen and other materials therein. The oxygen content is a function of both the blood volume and the concentration of the oxygen in the blood volume. The concentration of the oxygen in the blood volume is generally measured as blood oxygen saturation for reasons which are described in full in the above-identified issued U.S. Pat. Nos. 5,482,036 and 5,490,505. As further described in the two referenced patents, the blood oxygen saturation is determined by comparing the relative absorption of the red light and the infrared light in the finger 102. The comparison is complicated by the noise caused by movement, ambient light, light scattering, and other factors.

In FIG. 3, a pair of signals $S_1(t)$ and $S_2(t)$ represent the effect of the time-varying volume and scattering components of the blood in the finger 102 on the red light and the infrared light, respectively, passing through the finger 102 from the LEDs 106, 108 to the detector 150. The red light signal portion $S_1(t)$ is caused by the variable attenuation of the red light passing through the finger 102. The infrared light signal portion $S_2(t)$ is caused by the variable attenuation of the infrared light passing through the finger 102. To show the effect of the variable attenuations, the signal portion $S_1(t)$ is illustrated as being applied to a first attenuation modulator 191 which multiplies the signal $S_1(t)$ by the modulated red output $I_{RDMOD}(t)$ of the first modulator 190. Similarly, the infrared light signal portion $S_2(t)$ is illustrated as being applied to a second attenuation modulator 193 which multiplies the signal $S_2(t)$ by the modulated infrared output $I_{IRMOD}(t)$ of the second modulator 192. The outputs of the first and second attenuation modulators 191, 193 are provided to the receiving photodetector 150. The photodetector 150 is modeled as adder 194 and an adder 196. The outputs of the first and second attenuation modulators 191, 193 are provided to the adder 194 to generate a composite signal M(t) where:

$$M(t)=S_1(t)M_1(t)+S_2(t)M_2(t). \tag{1}$$

The signal M(t) from the adder 194 is provided to the adder 196 where the signal M(t) is added to a signal n(t) which represents a composite noise signal caused by ambient light, electromagnetic pickup, and the like, which are also detected by the photodetector 150. The output of the adder 196 is a signal M'(t)=M(t)+n(t) which includes noise components as well as the signal components. The noise components include DC components and harmonics of the power line frequency that appear in the ambient light. In addition, as will be discussed in more detail below, the signal M'(t) may also include noise at higher frequencies caused, for example, by other devices such as electrocauterization equipment, or the like.

The M'(t) signal output of the third adder 196 (i.e., the output of the detector 150) is applied to the input of the signal processing block 170. Within the signal processing block 170, the signal M'(t) is first passed through a fixed gain amplifier 197 and then through an analog bandpass filter 198. The analog bandpass filter 198 has a passband selected to pass signals in the range of 20 Hz to 10,000 Hz. Thus, the analog bandpass filter 198 removes a significant portion of the noise below 10 Hz. The signal components responsive to the blood oxygen saturation are frequency shifted by the operation of the two modulation signals $M_1(t)$ and $M_2(t)$ and are passed by the analog bandpass filter 198.

In the preferred embodiment, the output of the analog bandpass filter 198 is sampled by an analog-to-digital converter 199 and converted therein to digital signals. For example, the signals are preferably sampled at 46,875 samples per second. The output of the analog-to-digital converter 199 is a signal MF(k).

The signal MF(k) is provided as a first input to a first demodulating multiplier 210. The signal MF(k) is also provided as a first input to a second demodulating multiplier 212. A first demodulating signal $D_1(k)$ is provided as a second input to the first demodulating multiplier 210, and a second demodulating signal $D_2(k)$ is provided as a second input to the second demodulating multiplier 212. The output of the first demodulating multiplier 210 is provided as an input to a first lowpass filter 220, and the output of the second demodulating multiplier is provided as an input to a second lowpass filter 222. The bandwidths of the lowpass filters 220, 222 are preferably approximately 10 Hz.

The output of the first lowpass filter 220 is a signal $\hat{S}_1(t)$, which, as discussed below, is an estimate of the signal $S_1(t)$. The output of the second lowpass filter 222 is a signal $\hat{S}_2(t)$, which, as discussed below, is an estimate of the signal $S_2(t)$. As will be shown below, the selection of the first demodulating signal $D_1(k)$ and the second demodulating signal $D_2(k)$ in accordance with the present invention substantially reduces or eliminates the effects of noise in the two output signals $\hat{S}_1(t)$ and $\hat{S}_2(t)$ and also substantially reduces or eliminates crosstalk between the two signals.

In the preferred embodiment of the present invention, the sample rates of the outputs of the lowpass filter 220 and the lowpass filter 222 are compressed by respective sample rate compressors 221 and 223. In particular, the sample rate compressors 221, 223 reduce the sample rate by 750 to a sample rate of, for example, 62.5 Hz to provide an output which can be further processed in accordance with the methods and apparatuses described in the above-referenced patents. The sample rate compressions which occur in the sample rate compressors 221, 223 reduce the rate at which the output signals $\hat{S}_1(t)$ and $\hat{S}_2(t)$ need to be processed while maintaining the sample rate well above the 0–10 Hz frequency content of the signals of interest. The outputs of the filters 220, 222, or the sample rate compressors 221, 223, if included, are provided on respective output lines 224 and 226.

In order to facilitate an understanding of how the present invention operates in demodulating the output signal MF(k) from the analog-to-digital converter 199, the modulation signals $M_1(t)$ and $M_2(t)$ will first be described in terms of their frequency components. One skilled in the art will appreciate that the modulation signals $M_1(t)$ and $M_2(t)$ can each be represented as a Fourier cosine series expansion (e.g, $$\sum_{n=0}^{\infty} a_n \cos(n\omega t),$$

where $\omega=2\pi/T$) representing the fundamental and harmonic frequencies of the rectangular signal pulses. One skilled in the art will understand that the Fourier series expansion includes phases; however, by suitably selecting the time origin, the phases are set to zero. A component which is 180° out of phase with a corresponding component will advantageously be represented by a minus sign before the coefficient.

Figure 4:
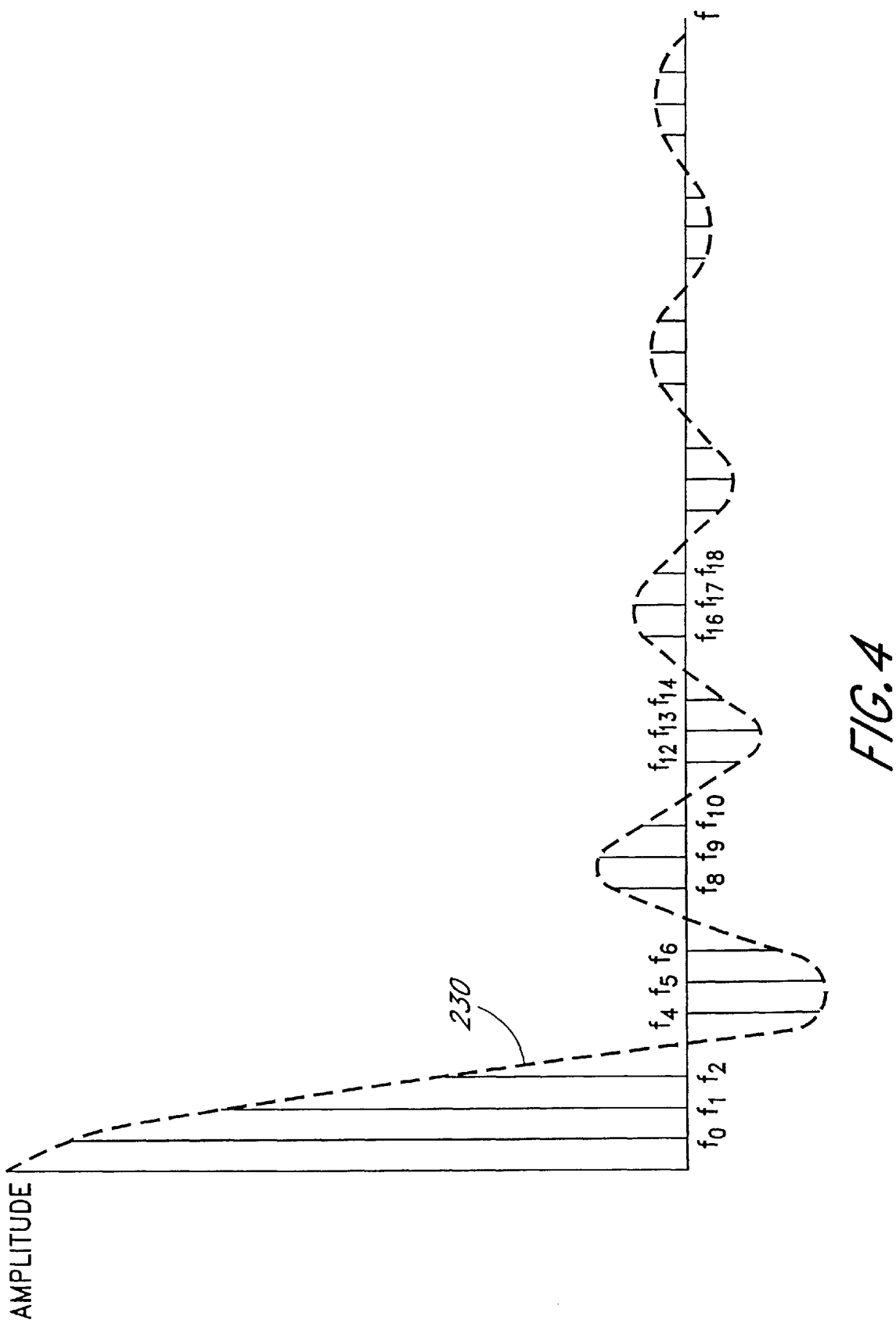
FIG. 4 illustrates a frequency spectra of the first modulation signal $M_1(t)$ for n=0, 1, 2, . . . , where the horizontal axis represents frequency and the vertical axis represents the energy in the DC and harmonic components of the signal.

FIG. 4 illustrates a frequency spectra of the first modulation signal $M_1(t)$ for n=0, 1, 2, . . . , where the horizontal axis represents frequency, with the energy in the DC component along the vertical axis and increasing harmonics of the fundamental frequency along the horizontal axis. The length of each component of $M_1(t)$ along the vertical axis represents the energy E(n) in each component of the frequency spectra. The first component to the right of the vertical axis is at the fundamental frequency (i.e., 1/T), which is designated herein as $f_0$; however, it should be understood that the fundamental frequency $f_0$ corresponds to n=1. The second component to the right of the vertical axis is the first harmonic $f_1$ (i.e., n=2), which has a frequency which is twice the fundamental frequency. The third component to the right of the vertical axis is the second harmonic $f_2$ (i.e., n=3), which has a frequency which is three times the fundamental frequency. The components to the right of the second harmonic are numbered accordingly. (Note, other conventions identify the fundamental frequency as the first harmonic, and designate the second harmonic as the frequency that is twice the fundamental frequency. The identification of the fundamental frequency as $f_0$ is used in the discussion that follows.)

In FIG. 4, a modulation envelope 230 is shown in dashed lines. The modulation envelope 230 represents the magnitudes of the fundamental and the harmonics of the signal $M_1(t)$. The shape of the envelope is determined by the modulation signal $M_1(t)$ which, for a repeating rectangular pulse train starting at time t=0 and having a normalized amplitude of 1, can be expressed as:

$$M_1(t) = \frac{\tau}{T} \sum_{n=0}^{\infty} \text{sinc}\left(\frac{n\tau}{T}\right)\cos\left(\frac{2\pi n t}{T}\right) \quad (2)$$

Where sinc is the function $(\sin \pi x)/\pi x$ (i.e., $\text{sinc}(n\tau/T)=\sin(n\pi\tau/T)(n\pi\tau/T)$). In the example shown, $\tau=\frac{1}{4}T$. (Note that for sampled signals, the envelope is more accurately represented as $\sin\alpha/\sin\beta$; however, as well known in the art, for the frequencies of interest, the sinc function is a suitable approximation.) Thus, the frequency spectra has nulls at n=4, n=8, n=12, and so on, corresponding to the third harmonic $f_3$, the seventh harmonic $f_7$, the eleventh harmonic $f_{11}$, and so on. Note that Equation 2 is an idealized form of the equation for $M_1(t)$, and that in general:

$$M_1(t) = \frac{\tau}{T} \sum_{n=0}^{\infty} a_n \text{sinc}\frac{n\tau}{T} e^{-j\omega_0 n t} \quad (3)$$

where $\alpha_n$ is a complex number. In the discussion that follows, the values of $\alpha_n$ are assumed to be real numbers only.

A similar frequency spectra (not shown) for the modulation signal $M_2(t)$ is determined by the expression:

$$M_2(t) = \frac{\tau}{T} \sum_{n=0}^{\infty} (-1)^n \text{sinc}\left(\frac{n\tau}{T}\right)\cos\left(\frac{2\pi n t}{T}\right) \quad (4)$$

An envelope for the frequency spectra of second modulation signal $M_2(t)$ will have the same magnitudes; however, it should be understood that because of the $(-1)^n$ term in the expression for $M_2(t)$, the fundamental $f_0$ and every even harmonic (i.e., $f_2$, $f_4$, etc.) are 180° out of phase with the corresponding harmonic of the first modulation signal $M_1(t)$.

In FIG. 3, the analog-to-digital converter 199 converts the signal M'(t) to a sequence of sampled digital values MF(k) at a sampling rate of, for example, 46,875 samples per second. As discussed above, the first demodulating multiplier 210 multiplies the output MF(k) of the converter 199 by the first demodulating signal $D_1(k)$ to generate the first output sequence $\hat{S}_1(k)$, and the second demodulating multiplier 212 multiplies the output MF(k) by the second demodulating signal $D_2(k)$ to generate the second output sequence $\hat{S}_2(k)$. The multiplication by the multipliers 210, 212 can also be expressed as follows:

$$\hat{S}_1(k) = LP[MF(k)D_1(k)] \tag{5}$$

and $$\hat{S}_2(k) = LP[MF(k)D_2(k)] \tag{6}$$

where LP is the transfer function of the lowpass filter 220 and of the lowpass filter 222. If, for simplicity, the noise is assumed to be zero, then:

$$M'(t) = S_1(t)M_1(t) + S_2(t)M_2(t) \tag{7}$$

Therefore:

$$\hat{S}_1(k) = LP[[S_1(k)M_1(k) + S_2(k)M_2(k)]D_1(k)] \tag{8}$$

and thus $$\hat{S}_1(k) = LP[[S_1(k)M_1(k)]D_1(k) + [S_2(k)M_2(k)]D_1(k)] \tag{9}$$

Similarly:

$$\hat{S}_2(k) = LP[[S_2(k)M_2(k)]D_2(k) + [S_1(k)M_1(k)]D_2(k)] \tag{10}$$

Since LP is a linear operator, the right-hand side of Equations 9 and 10 can be split into two terms. The first term on the right-hand side of each of Equations 9 and 10 above is the desired signal portion of the equation, and the second term on the right-hand side of each of the equations is the crosstalk portion. Thus, in order to reduce the crosstalk to zero, the second term of each of Equations 9 and 10 is set to zero:

$$LP[S_2(k)M_2(k)D_1(k)] = 0 \tag{11}$$

and $$LP[S_1(k)M_1(k)D_2(k)] = 0 \tag{12}$$

By setting the second terms to zero, Equations 9 and 10 reduce to:

$$\hat{S}_1(k) = LP[S_1(k)M_1(k)D_1(k)] \tag{13}$$

and $$\hat{S}_2(k) = LP[S_2(k)M_2(k)D_2(k)] \tag{14}$$

One goal of the present invention is to select the demodulating signals $D_1(k)$ and $D_2(k)$ to satisfy Equations 11 and 12 to thereby reduce Equations 9 and 10 to Equations 13 and 14. This is accomplished by utilizing Equations 2 and 3 to simplify the two equations by selectively using components of the two modulating signals $M_1(t)$ and $M_2(t)$ to generate the demodulating sequences $D_1(k)$ and $D_2(k)$.

In order to simplify the discussion, Equation 2 can be rewritten as:

$$M_1(t) = \sum_{n=1}^{\infty} E(n)\cos(n\omega t) \tag{15}$$

where E(n) is the sinc envelope for the fundamental frequency $f_0(n=1)$ and the harmonics $f_1(n=2)$, $f_2(n=3)$, and so on, where cos(nωt) represents the cosine term cos(2πnt/T), where ω=2π/T. (Note, as discussed above, for discrete sampled signals, the actual envelope of E(n) is a sin α/sin β function; however, for the frequencies of interest, the sinc function is a suitable representation.)

As discussed above, the DC term (n=0) does not need to be considered because of the operation of the filter 198, and the analog-to-digital converter 199, as well as the action of the demodulation, which shift any unwanted DC or low frequency signals having a frequency less than approximately 10 Hz (hereinafter near-DC signals) to higher frequencies before lowpass filtering. As a further simplification, the magnitude of the fundamental term in Equation 15 is normalized to a value of 1 (i.e., E(1)=1). Note that the normalization results in the need for a scale factor, which will be discussed below. Thus, Equation 15 becomes:

$$M_1(t) = \cos \omega t + a \cos 2\omega t + b \cos 3\omega t + c \cos 4\omega t + \ldots \tag{16}$$

The demodulation signal $D_1(t)$ is defined as:

$$D_1(t) = \cos \omega t + B \cos 2\omega t \tag{17}$$

For reasons set forth below, only the first two cosine terms are needed.

Similarly, the second modulating signal $M_2(t)$ becomes:

$$M_2(t) = -\cos \omega t + a \cos 2\omega t - b \cos 3\omega t + c \cos 4\omega t + \ldots \tag{18}$$

and the second demodulating signal $D_2(t)$ is defined as:

$$D_2(t) = -\cos \omega t + B \cos 2\omega t \tag{19}$$

Note that the signs of the fundamental and odd harmonics in Equation 18 are 180° out of phase with the corresponding terms in Equation 16.

Note, as will be developed more fully below, by including only the fundamental (cos ωt) and the first harmonic (cos 2ωt) in each of the demodulation signals, only the signals proximate to the fundamental and first harmonic need to be considered. By eliminating higher harmonics, the effects of the higher harmonics of the power line frequency are also eliminated in the output signals generated by the present invention.

Assume that the filter 198 and the analog-to-digital converter 199 do not affect the magnitude of the signal MF(k) with respect to M'(t) for the frequencies having significant energy. Therefore, starting with Equation 7 above, M'(t) can be written as:

$$M'(t) = S_1(t)[\cos \omega t + a \cos 2\omega t + b \cos 3\omega t + \ldots] + S_2(t)[-\cos \omega t + a \cos 2\omega t - b \cos 3\omega t + \ldots] \tag{20}$$

When the first demodulating multiplier 210 multiplies M'(t) by $D_1(t)$, the terms on the right-hand side of Equation 20 are multiplied by the terms on the right-hand side of Equation 17. Thus:

$$M'(t)D_1(t) = S_1(t)[\cos \omega t + a \cos 2\omega t + b \cos 3\omega t + \ldots][\cos \omega t + B \cos 2\omega t] + S_2(t)[-\cos \omega t + a \cos 2\omega t - b \cos 3\omega t + \ldots][\cos \omega t + B \cos 2\omega t] \tag{21}$$

The term $S_1(t)[\cos \omega t + a \cos 2\omega t + b \cos 3\omega t + \ldots][\cos \omega t + B \cos 2\omega t]$ is the signal term which is to be preserved, and the term $S_2(t)[-\cos \omega t + a \cos 2\omega t - b \cos 3\omega t + \ldots][\cos \omega t + B \cos 2\omega t]$ is the crosstalk term to be eliminated.

Expanding the crosstalk term from Equation 21, generates:

$$\text{crosstalk} = S_2(t)[-\cos^2 \omega t - B \cos \omega t \cos 2\omega t + a \cos 2\omega t \cos \omega t + aB \cos^2 2\omega t - b \cos 3\omega t \cos \omega t - bB \cos 3\omega t \cos 2\omega t + \ldots] \quad (22)$$

Using the identity, $\cos(x)\cos(y) = \frac{1}{2}[\cos(x+y) + \cos(x-y)]$, the crosstalk term from Equation 22 becomes:

$$\text{crosstalk} = S_2(t)[-\frac{1}{2}(\cos 2\omega t + 1) + ((a-B)/2)[\cos 3\omega t + \cos \omega t] + (aB/2)[\cos 4\omega t + 1] - (b/2)[\cos 4\omega t + \cos 2\omega t] - (bB/2)[\cos 5\omega t + \cos \omega t] + \ldots] \quad (23)$$

The remaining terms in Equation 23 will all have a factor of $\cos \omega t$ or higher. Thus, Equation 23, when fully expanded only includes near-DC terms:

$$\text{crosstalk}_{DC} = LP[S_2(t)[(aB/2) - \frac{1}{2}]] \quad (24)$$

where $S_2(t)$ corresponds to the infrared portion of the original plethysmograph signal which has a bandwidth of interest of approximately 0 to 10 Hz. Any components present above 10 Hz will be eliminated by the action of the lowpass filter 220. Thus, it can be seen that only the signals of interest are folded back to DC or near-DC. By using the lowpass filter 220, the DC terms and near-DC terms can be isolated so that only the DC terms and near-DC terms of the crosstalk are presented at the output of the lowpass filter 220. Thus, in order to eliminate the crosstalk, the crosstalk terms in Equation 24 need to be set to zero:

$$LP[S_2(t)[aB/2 - \frac{1}{2}]] = 0 \quad (25)$$

Thus:

$$B = 1/a \quad (26)$$

The result in Equation 26 can also be expressed using a geometric interpretation of vector projection (i.e., dot products) of $S_2(t)$ and $S_1(t)$ wherein the projection of $S_2(t)$ onto $D_1(t)$ is equal to zero and the projection of $S_2(t)$ onto $D_2(t)$ is maximized. In other words, express $S_1(t)$, $S_2(t)$, $D_1(t)$ and $D_2(t)$ as vectors of samples in an n-dimensional sample space (e.g., $S_1(t)$ is represented as a vector $S_1$ of samples $S_1(k)$). For example, in a preferred embodiment, n=148, and thus $S_1$, $S_2$, $D_1$ and $D_2$ are vectors of 148 samples each. The first crosstalk term is $S_1 \cdot D_2$. The second crosstalk term is $S_2 \cdot D_1$. The first signal output is $S_1 \cdot D_1$. The second signal output is $S_2 \cdot D_2$. Select the vectors $D_1$ and $D_2$ to drive the crosstalk terms to zero.

The relationship in Equation 26 also works to preserve the signal term. In particular, the signal term in Equation 21 can be expanded and lowpass filtered in the same manner as the crosstalk term to obtain:

$$\text{signal} = \hat{S}_1(t) = LP[S_1(t)[(aB/2) + \frac{1}{2}]] \quad (27)$$

Using the relationship from Equation 26, then Equation 27 becomes:

$$\text{signal} = \hat{S}_1(t) = LP[S_1(t)[(a/2a) + \frac{1}{2}]] = LP[S_1(t)] = S_1(t) \quad (28)$$

It can be readily shown that the same relationship holds for the crosstalk term and the signal term for the signal $S_2(t)$ by defining the second demodulation signal $D_2(t)$ as:

$$D_2(t) = -\cos \omega t + B \cos 2\omega t \quad (29)$$

and multiplying $M_2(t)$ by $D_2(t)$. After expanding the crosstalk and signal terms and eliminating the terms above 10 Hz, it can be shown that by selecting $B = 1/a$, the crosstalk term is canceled and the signal term $S_2(t)$ is recovered.

From the foregoing, it can be seen that by choosing the relationship between the magnitude of B as the reciprocal of a, then the crosstalk terms are eliminated and the signal terms are preserved. Note that neither A nor B is an absolute value. As set forth in Equation 16, a is the magnitude of the $\cos 2\omega t$ term of $M_1(t)$ when the magnitude of the $\cos \omega t$ term of $M_1(t)$ is normalized to 1. Similarly, from Equation 17, B is the magnitude of the $\cos 2\omega t$ term of $D_1(t)$ when the $\cos \omega t$ term of $D_1(t)$ is normalized to 1.

Figure 5:
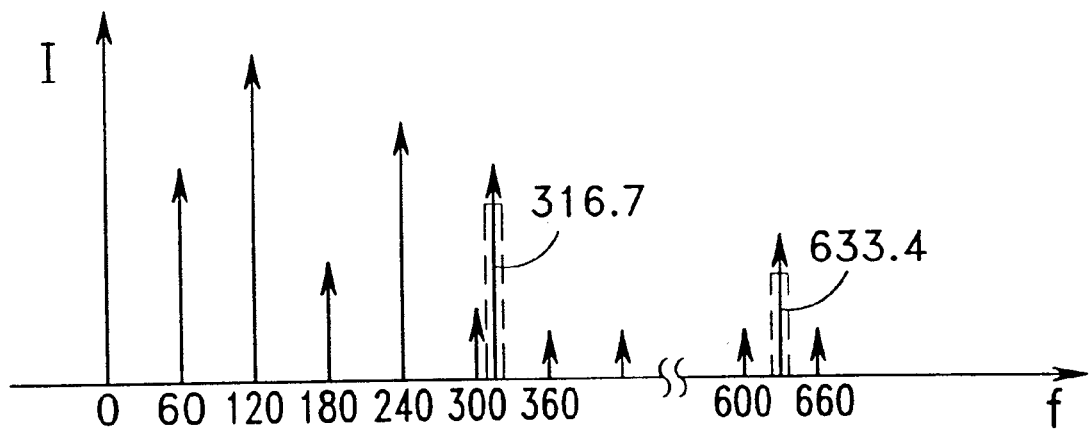
FIG. 5 illustrates an exemplary spectrum of the first and second harmonics of the present invention when the fundamental frequency is selected to be 316.7 Hz in comparison to the fundamental and harmonics of conventional 60 Hz power.

It should be understood that both $D_1(t)$ and $D_2(t)$ can include higher harmonic terms; however, such additional terms could result in increased sensitivity to the noise of fluorescent lights and the like because of the harmonics of the 60 Hz power line frequency (or the 50 Hz power line frequency in other countries). For example, FIG. 5 illustrates an exemplary spectrum of the first and second harmonics of the present invention when the fundamental frequency is selected to be 316.7 Hz. Thus, the first harmonic frequency is 633.4 Hz. Note that the variations in the signals caused by blood flow throughout a cardiac cycle causes the fundamental and harmonics of modulation frequency to be surrounded by sidebands representing the frequency content of the plethysmograph. For example, in FIG. 5, the first and second harmonics are at 316.7 Hz and 633.4 Hz, ±10 Hz.

As further illustrated in FIG. 5, the conventional 60 Hz power line frequency has harmonics at 120 Hz, 180 Hz, 240, etc. Thus, the nearest harmonics of the power line frequency to the first harmonic of the present invention are at 300 Hz and 360 Hz, and the nearest harmonics of the power line frequency to the second harmonic of the present invention are 600 Hz and 660 Hz. Similarly, if used in a country having a 50 Hz power line frequency, the nearest harmonics to the first harmonic of the present invention are 300 Hz and 350 Hz, and the nearest harmonics to the second harmonic of the present invention are 600 Hz and 650 Hz. Even if the power frequency were to vary by up to 1.5 percent, the noise generated by the ambient light from fluorescent lamps, or the like, would not be at the first and second harmonic frequencies of the present invention. The fundamental frequency has thus been selected to avoid power line caused ambient noise at the first and second harmonic frequencies.

The foregoing discussion assumed that the filter 198 did not significantly affect the amplitude of the filtered signal. If the filter 198 does have an affect on the amplitude, then B will be a constant times the value of B determined above:

$$B = k/a \quad (30)$$

where k depends on the relative attenuation of the first harmonic and the second harmonic through the filter 198.

Although the value of the coefficient B can be calculated as set forth above, the calculations may be complicated if the filter 198 or the modulators 190, 192 introduce phase changes which cause the calculations to be performed on complex numbers. For example, if the modulation signals $M_1(t)$ and $M_2(t)$ are not rectangular waves which have 25% duty cycles and which are precisely 180° out of phase, as illustrated herein, then the coefficients of the frequency components of the modulation signals may be complex to account for the phase relationships, and thus, the coefficients of the demodulation signals may be complex.

Figure 2:
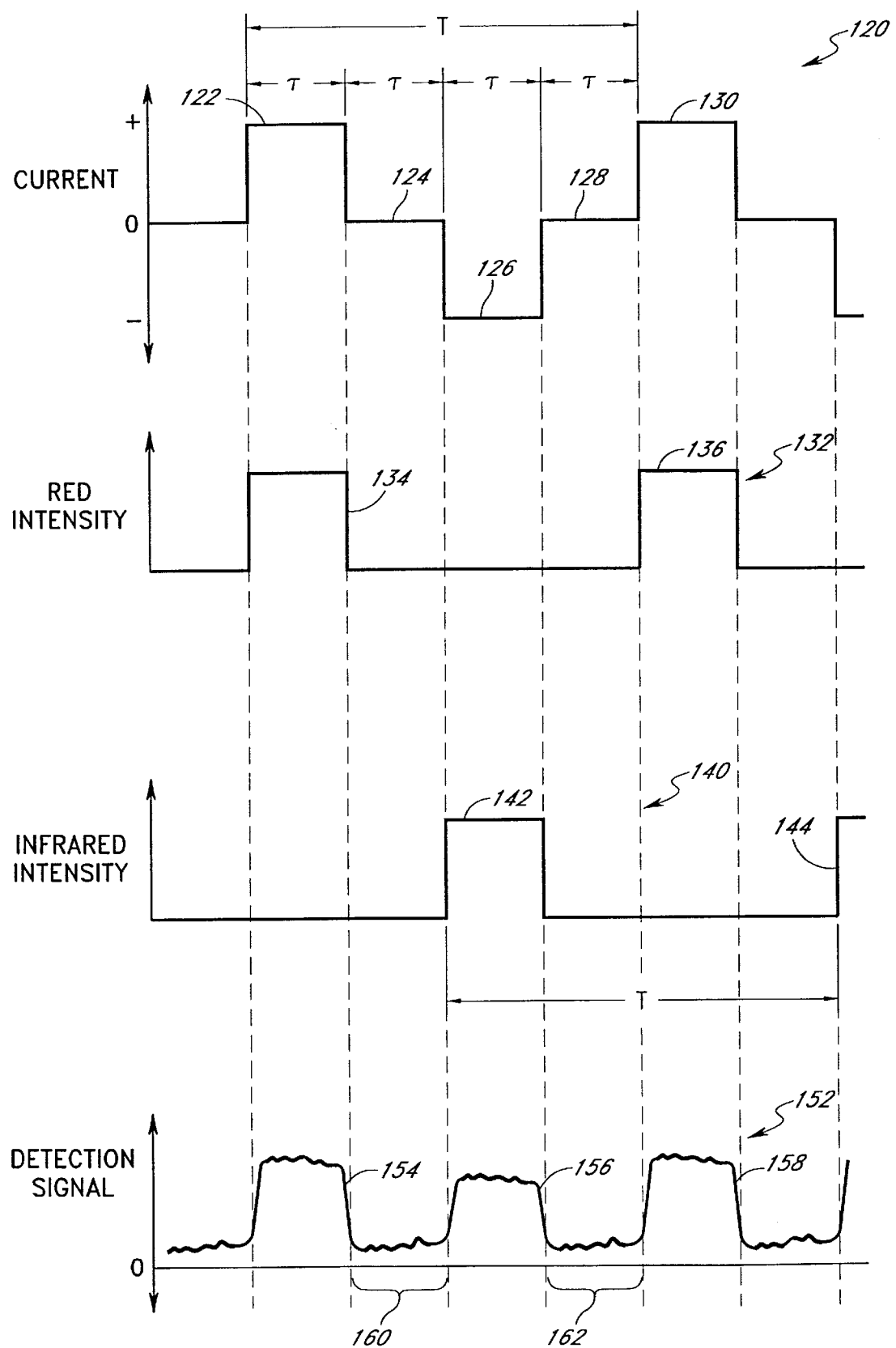
FIG. 2 illustrates exemplary waveforms of the current through the LEDs in FIG. 1 and the resulting intensities of the red light and the infrared light generated by the LEDs.
Figure 6:
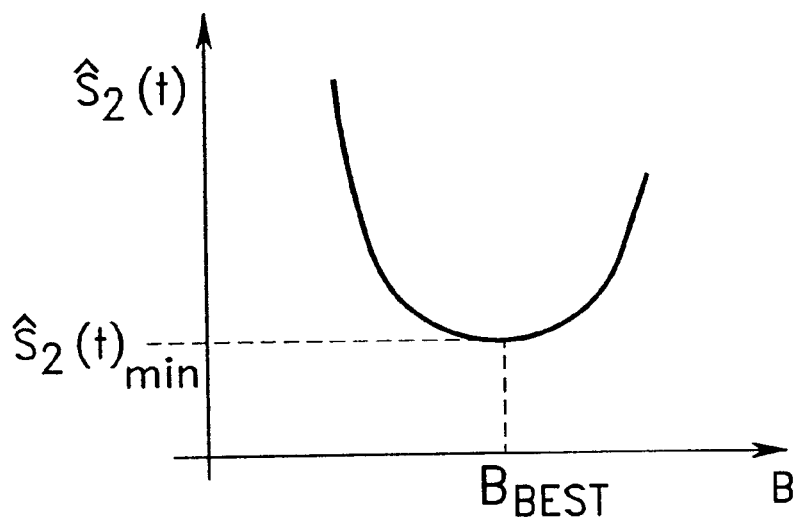
FIG. 6 illustrates the effect of the value of B on the measured signal output $\hat{S}_2(t)$ responsive to the red modulation pulses as the value of B is varied while the infrared modulation pulses are off.

As illustrated in FIG. 6, the value of B can also be determined empirically by performing a initial measurement with one channel (i.e., either the red pulse or the infrared pulse turned off) and minimizing the crosstalk. In particular, during the initial measurement, the waveform 140 in FIG. 2 is set to a continuous zero value so that no infrared pulses are generated. Thus, the detector 150 (FIG. 1) receives only the light generated by the red LED 106. Thus, $M_2(t)$ is set to zero, and Equation 10 for $\hat{S}_2(t)$ becomes:

$$\hat{S}_2(t) = LP[S_1(t)M_1(t)D_2(t)] \quad (31)$$

It can be seen that $\hat{S}_2(t)$ includes only a crosstalk portion, which can be measured on the output from the second lowpass filter 222. Thus, by varying the value B while monitoring the magnitude or the RMS (root-mean-squared) value of the output signal $\hat{S}_2(t)$, a minimum magnitude $\hat{S}_2(t)_{min}$ for the output signal $\hat{S}_2(t)$ can be found which corresponds to the best value $B_{BEST}$ for B. In an ideal system, the best value for B corresponds to a zero value for the output signal $\hat{S}_2(t)$; however, in a real environment, the best value of B may correspond to a non-zero value for $\hat{S}_2(t)$ (i.e., a minimum error for $\hat{S}_2(t)$). It should be understood that the value of $B_{BEST}$ can also be determined by turning off the red LED 106 and varying B while monitoring $\hat{S}_1(t)$ until $\hat{S}_1(t)$ is minimized.

From the foregoing, it can be seen that the effect of the modulation signals $D_1(t)$ and $D_2(t)$ is to shift the DC or near-DC noise terms up in frequency while shifting the signals of interest at the harmonics back to DC or near-DC, which in effect interchanges the noise spectra and the signal spectra so that the noise spectra can be eliminated by the action of the lowpass filters 220, 222, leaving only the signals of interest.

Figure 7:
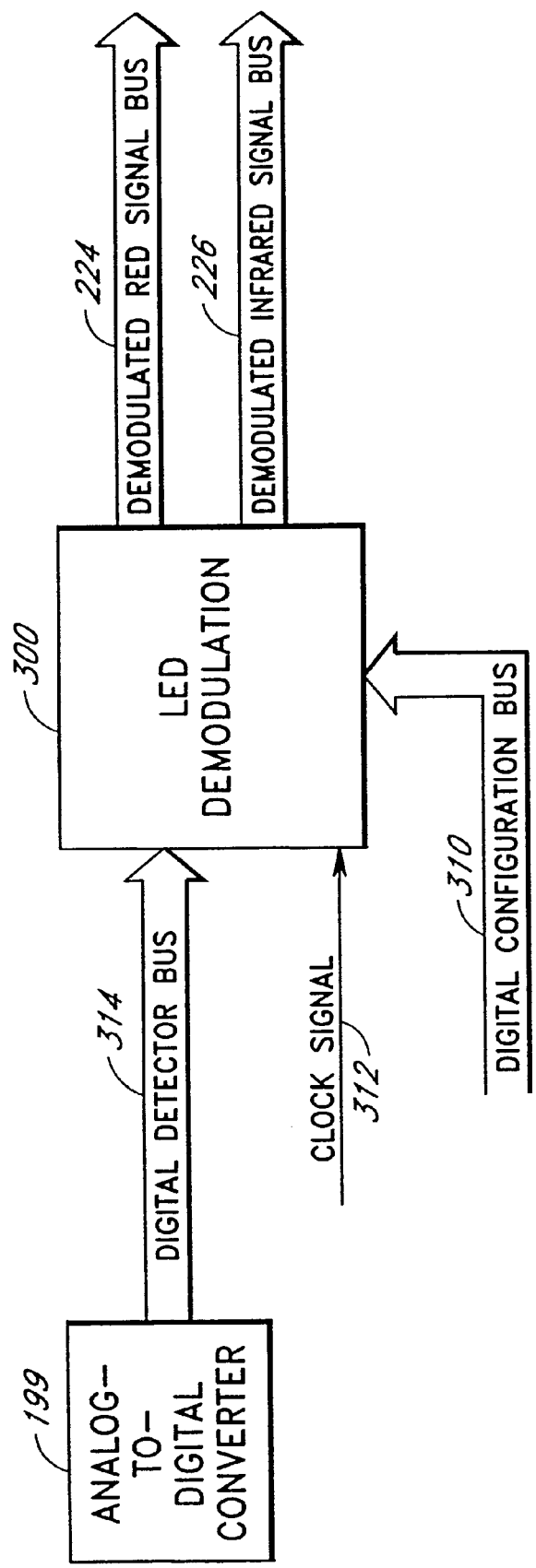
FIG. 7 illustrates a preferred embodiment of the present invention implemented in a digital processing system.

FIG. 7 illustrates a preferred embodiment of the present invention which implements the functions described above in a digital system. Preferably, the digital system comprises a digital signal processor (not shown), and the blocks described herein comprise data structures within the digital signal processor and software routines that implement the processes described below. In particular, the present invention comprises an LED demodulation block 300 which receives a digital configuration signal on a bus 310, a clock signal on a line 312 and a digital detector signal on a bus 314 as inputs. The digital configuration signal bus 310 provides a way to change the configuration of the LED demodulation block 300 to accommodate different LEDs and different detection algorithms. Preferably, the clock signal on the line 312 is a 46,875 Hz (46.875 kHz) square wave signal which is used to synchronize the timing functions of the present invention. The digital detector signal on the line 314 is the output of the analog-to-digital converter 199. The analog-to-digital converter 199 is connected to the output of the detector 150 (via the amplifier 197 and the filter 198) and samples the output of the detector 150 at 46,875 samples per second to provide a stream of sampled digital values of the red light and infrared light incident on the detector 150.

Figure 8:
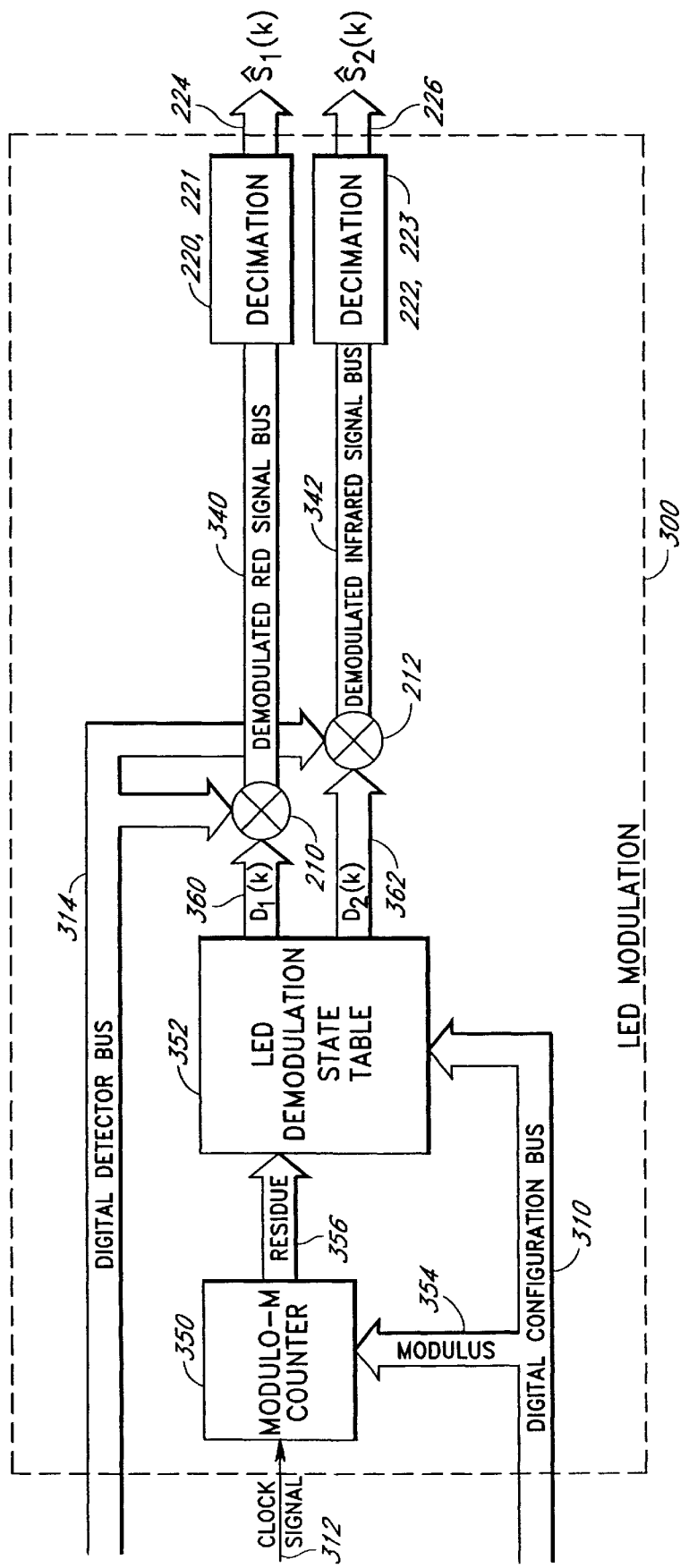
FIG. 8 illustrates a detailed block diagram of the demodulation portion of the present invention.

The LED modulation block 300 generates a demodulated red signal output on a bus 340 and generates a demodulated infrared signal output on a bus 342. The demodulated red signal output is passed through the low pass filter 220 and is output therefrom as the signal $\hat{S}_1(t)$. The demodulated infrared signal output is passed through the low pass filter 222 and is output therefrom as the signal $\hat{S}_2(t)$. As further illustrated in FIG. 8, the LED demodulation block 300 comprises a modulo-M block 350, an LED demodulation state table block 352, the first demodulating multiplier 210 and the second demodulating multiplier 212.

The modulo-M block 350 receives the main 46,875 Hz clock signal on the line 312 as one input and receives a MODULUS signal on a bus 354 as a second input. The bus 354 forms a portion of the configuration bus 310. The modulo-M block 350 divides the clock signal by the MODULUS signal and generates a RESIDUE signal (described below) on a bus 356 which is provided as one input to the LED modulation state table block 352. The LED modulation state table block 352 also receives the configuration signals on the configuration bus 310.

The LED demodulation state table is responsive to the residue signal and the configuration signals to generate the first demodulating signal $D_1(t)$ on a bus 360 and to generate the second demodulating signal $D_2(t)$ on a bus 362. The first demodulating signal $D_1(t)$ is provided as one input to the first demodulating multiplier 210, as described above. The second demodulating signal $D_2(t)$ is provided as one input to the second demodulating multiplier 212, as described above. The first demodulating multiplier 210 and the second demodulating multiplier 212 receive the digital detector signal on the line 314 as respective second inputs. The demodulating multipliers 210, 212 multiply the digital detector signal by the first demodulating signal $D_1(t)$ and the second demodulating signal $D_2(t)$, respectively, to generate a demodulated red signal and a demodulated infrared signal on the buses 340 and 342, respectively. Because the outputs of the two demodulating multipliers 210 and 212 include the terms $\cos \omega t$, $\cos 2\omega t$, and higher, the demodulated signals on the buses 340 and 342 are provided as respective inputs to the low pass filters 220 and 222 to pass only the near-DC terms, as discussed above. The outputs of the lowpass filters 220 and 222 on the buses 344 and 346, respectively, are the $\hat{S}_1(t)$ signal and the $\hat{S}_2(t)$ signal which contain only the near-DC terms, which, in accordance with the discussion presented above represent the original input signals $S_1(t)$ and $S_2(t)$ with the unwanted noise substantially reduced or eliminated. The two signals $\hat{S}_1(t)$ and $\hat{S}_2(t)$ are then applied to computation circuitry (not shown) which computes the blood oxygen saturation and other cardiographic parameters in a manner described in the above-cited U.S. Pat. Nos. 5,482,036 and 5,490,505.

Figure 9:
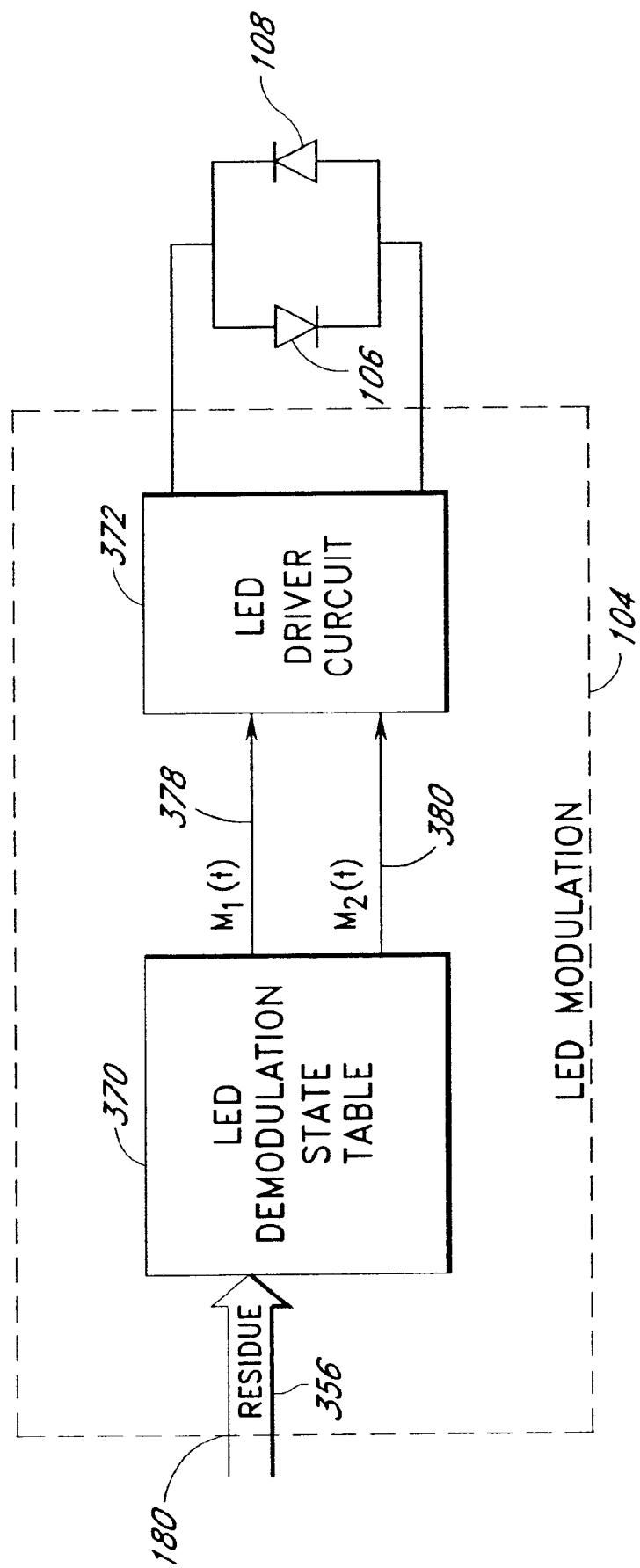
FIG. 9 illustrates a detailed block diagram of the modulation portion of the present invention.

The residue signal generated as the output from the modulo-M block 350 is a multiple bit signal that counts from 0 to MODULUS-1. In the preferred embodiment described herein, MODULUS has a value of 148. Thus, the RESIDUE output of the modulo-M block 350 counts from 0 to 147. The RESIDUE output of the modulo-M block 350 is a number that is provided as the input to the LED demodulation state table block 352. As illustrated in FIG. 9, the RESIDUE output on the bus 356 corresponds to the signal 180 in FIG. 1 and is also provided to the input of an LED modulation state table block 370 which, together with an LED driver circuit 372, comprise the modulation block 104 (FIG. 1) which generates the drive signals to the red LED 106 and the infrared LED 108. As described above, the red LED 106 and the infrared LED 108 generate the modulation signals $M_1(t)$ and $M_2(t)$, respectively, which effectively operate as carriers for the plethysmograph waveform to be measured. In particular, as illustrated by a red drive timing waveform 374 and by a infrared drive timing waveform 376 in FIG. 10, the modulation state table block 370 generates a red signal pulse 378 during the time when the RESIDUE signal increments from 0 to 36. Then, the modulation state table block 370 generates neither a red signal pulse nor an infrared signal pulse during the time when the RESIDUE signal increments from 37 to 73. Then, the modulation state table block 370 generates the infrared signal pulse 380 during the time when the RESIDUE signal increments from 74 to 110. Then, the modulation state table block 370 again generates neither a red signal pulse nor an infrared signal pulse during the time when the RESIDUE signal increments from 111 to 147. The RESIDUE signal then resets to 0 and the process repeats continuously.

The red signal pulse 378 and the infrared signal pulse 380 from the modulation state table block 370 are provided as inputs to the LED driver circuit 372 which turns on the red LED 106 when the red signal pulse 376 is active and turns on the infrared LED 108 when the infrared signal pulse 378 is active by generating the current waveform 120 illustrated in FIG. 2. The circuitry for converting the red signal pulse 376 and the infrared signal pulse 378 to the bi-directional current pulses of the waveform 120 is conventional and does not need to be described herein.

In the preferred embodiment, the LED demodulation state table block 352 implements demodulation equations which generally correspond to the Equations 17 and 19 described above. In particular, the LED demodulation state table block 352 receives the RESIDUE as one input to the state table and steps through the state table based upon the current value of the RESIDUE. The LED demodulation state table block 352 generates two output values for each value of the RESIDUE, wherein the first output value is the first demodulation signal $D_1(t)$ on the signal bus 360, and the second output value is the second demodulation signal $D_2(t)$ on the signal bus 362.

In particular, the LED demodulation state table block 352 implements the following forms of the demodulation signal $D_1(t)$ and the $D_2(t)$ equations:

$$D_1(t) = -SCL\left(\cos\left[2\pi t\left(\frac{R - 18.5 - HW\Delta}{Modulus}\right)\right] + HWD\left(\cos\left[4\pi t\left(\frac{R - 18.5 - HW\Delta}{Modulus}\right)\right]\right)\right) \quad (32)$$

and $$D_2(t) = -SCL\left(\cos\left[2\pi t\left(\frac{R - 18.5 - HW\Delta}{Modulus}\right)\right] - HWD\left(\cos\left[4\pi t\left(\frac{R - 18.5 - HW\Delta}{Modulus}\right)\right]\right)\right) \quad (33)$$

In Equations 32 and 33, the value SCL is a scale factor which determines the magnitudes of the two demodulation signals and which is used to compensate for the normalization discussed above and to compensate for other factors, such as, for example, non-ideal rectangular pulses. The method of determining the scale factor will be set forth below. In one particularly preferred embodiment, the value of SCL is 2.221441469. The value HWD is a hardware distortion factor, which corresponds to the value of B discussed above. The determination of the value B was described above, and will be described again below in connection with this preferred embodiment. In one particularly preferred embodiment where the pulses applied to the red LED 106 and the infrared LED 108 are idealized rectangular waves having 25% duty cycles, the value of HWD can be calculated to be 1.414213562. This ideal value for HWD can be determined by recognizing that the value of the coefficient A for the cos 2ωt terms in Equations 16 and 18 is determined by the sinc function. When the coefficient of the cos ωt term is normalized to 1, as in the two equations, then the value of the coefficient a is equal to √2/2. Thus, the ideal value for B (i.e., HWD) is √2. Of course, the actual value of the coefficient B, and thus HWD, will vary when the red pulses and the infrared pulses are not true rectangular waves. Since, in actual embodiments, the pulses will have finite rise times and fall times, the optimum value of HWD is preferably found empirically in the manner described below.

The value 18.5 in Equations 32 and 33 is used to align the demodulation waveforms with the modulation waveforms so that the peak of the cosine functions corresponds to the midpoints of each of the modulation waveforms. The value HWΔ is a hardware delay factor which may be needed in certain embodiments to compensate for delays in the analog processing, the digital processing or both, which cause the demodulation signals $D_1(t)$ and $D_2(t)$ to be out of phase with the modulation signals $M_1(t)$ and $M_2(t)$. In an ideal environment, the value of the hardware delay factor is 0. However, in one particularly preferred embodiment, the value of the hardware delay factor is 39. The modulus was described above and is basically the number of steps in each period of the waveforms. In the embodiment described herein, the modulus is 148. The value R is the RESIDUE, which varies from 0 to modulus-1, and thus, in the preferred embodiment, R varies from 0 to 147.

In operation, the clock signal on the line 312 causes the modulo-M block 350 to generate the RESIDUE signal, as described above. The RESIDUE value is applied to the LED modulation block 104 which generates the modulation signals $M_1(t)$ and $M_2(t)$, as described above. The RESIDUE value is also applied to the LED demodulation state table block 352 which generates a new value for $D_1(t)$ and a new value for $D_2(t)$ for each new RESIDUE value. Thus, 148 values of $D_1(t)$ and $D_2(t)$ are generated for each complete cycle. Because the clock signal is operating at 46,875 Hz, the modulation signals $M_1(t)$ and $M_2(t)$ and the demodulation signals $D_1(t)$ and $D_2(t)$ have a fundamental frequency of 316.722973 Hz, which, as discussed above, does not correspond to any harmonic of conventional 50 Hz or 60 Hz power line frequencies.

The HWΔ (hardware delay factor) value, the HWD (hardware distortion factor) value and the SCL (scaling factor) value are found empirically as follows. First, the ideal values of the hardware delay factor, the hardware distortion factor and the scale factor are applied to the Equations 32 and 33 in the LED demodulation state table block 352 (i.e., HWΔ=0, HWD=1.414213562, and SCL=2.221441469). To determine the optimum value of the hardware delay factor, the second modulation signal $M_2(t)$ is set to a constant value of zero (i.e., the infrared LED is maintained in its OFF state). The red LED pulses are applied as set forth above, and the digital detector output signal from the analog-to-digital converter is monitored and compared to the modulation signal $M_1(t)$. The relative delay between the beginning of the modulation signal $M_1(t)$ and the detection of the beginning of the responsive output from the analog-to-digital converter is the optimum hardware delay factor (HWΔ) value. In one exemplary embodiment, the optimum value of the hardware delay factor is 39.

After determining the value of the hardware delay factor and applying it to Equations 32 and 33, the ideal value of the hardware distortion factor and the ideal value of the scale factor are applied to the two equations. Again, with the red LED pulses applied to the red LED 106 and no pulses applied to the infrared LED, the value of the hardware distortion factor is slowly varied from its ideal value while the DC component of the demodulated infrared signal output on the line 342 is monitored. The value of the hardware distortion factor is varied until the measured DC component is minimized, and the value of the hardware distortion factor corresponding to the minimal DC component is selected as the optimum value for the hardware distortion factor.

Next, with the value of the hardware delay factor and the value of the hardware distortion factor set to their respective optimum values, as determined above, the value of the scale factor (SCL) is initially set to 1. Again, with the modulation system generating pulses only to the red LED 106, the DC component of the demodulated red signal output on the line 340 is measured. In addition, the difference in amplitude between the on state and the off state of the digital detector signal from the filter 198 is measured. The ratio of the measured amplitude difference to the measured DC component of the demodulated red signal output is selected as the optimum value for the scale factor.

Figure 10:
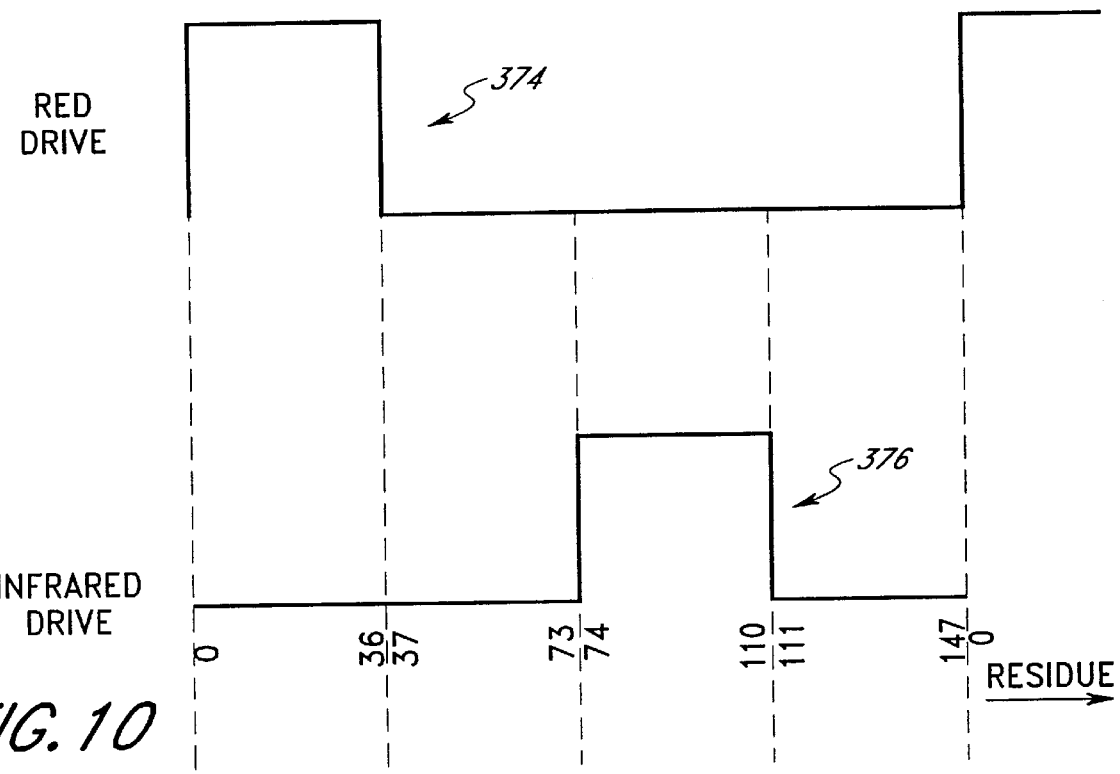
FIG. 10 illustrates the red drive waveform and the infrared drive waveform generated by the modulation portion of FIG. 9.
Figure 11:
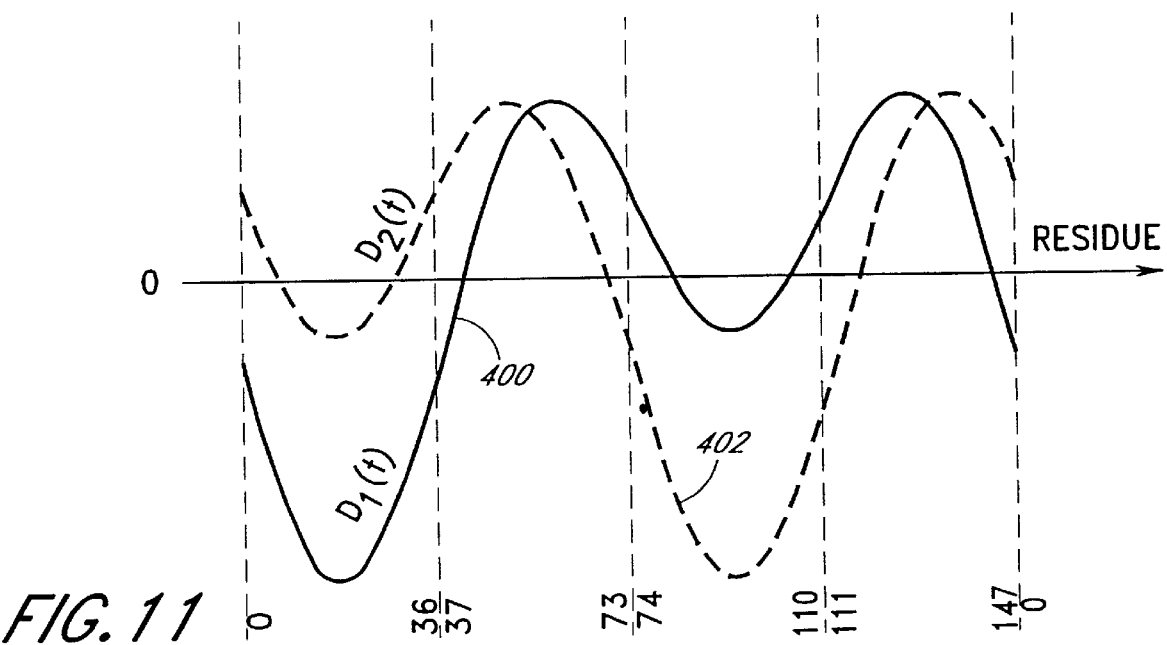
FIG. 11 illustrates the demodulation waveforms generated by the demodulation portion of FIG. 8.

An exemplary demodulation waveform $D_1(t)$ is illustrated by a waveform 400 in FIG. 11 and an exemplary demodulation waveform $D_2(t)$ is illustrated by a waveform 402 in FIG. 11. The demodulation waveforms in FIG. 11 are illustrated with the hardware delay factor set to 0 in order to align the waveforms with the modulation waveforms in FIG. 10. It should be understood that when the hardware delay factor is non-zero, the demodulation waveforms in FIG. 11 will be shifted in phase with respect to the modulation waveforms in FIG. 10.

Although described above in connection with the variation of the amplitude of the first harmonic component of the demodulation signals in order to minimize the crosstalk, it should be understood that the relative amplitude of the second harmonic component of the demodulation signals with respect to the amplitude of the fundamental component of the demodulation signals is determined by the relationship of the amplitude of the first harmonic component of the modulation signals to the amplitude of the fundamental component of the modulation signals. The relationship of the amplitude of the first harmonic component of the modulation signals depends in part upon the duty cycles of the modulation signals. If the modulation duty cycles are varied, the amplitude of the first harmonic component of the modulation signals changes. Thus, the crosstalk may also be minimized by holding the amplitudes of the components of the demodulation signals constant while varying the duty cycles of the modulation signals. One skilled in the art will appreciate that other variations in the modulation and demodulation signals may also be used to minimize the crosstalk between the two output signals.

A plurality of signals $S_1, S_2, S_3 \ldots S_n$ can be demodulated and the crosstalk between signals reduced to a minimum by application of the foregoing invention to more than two signals.

Figure 12:
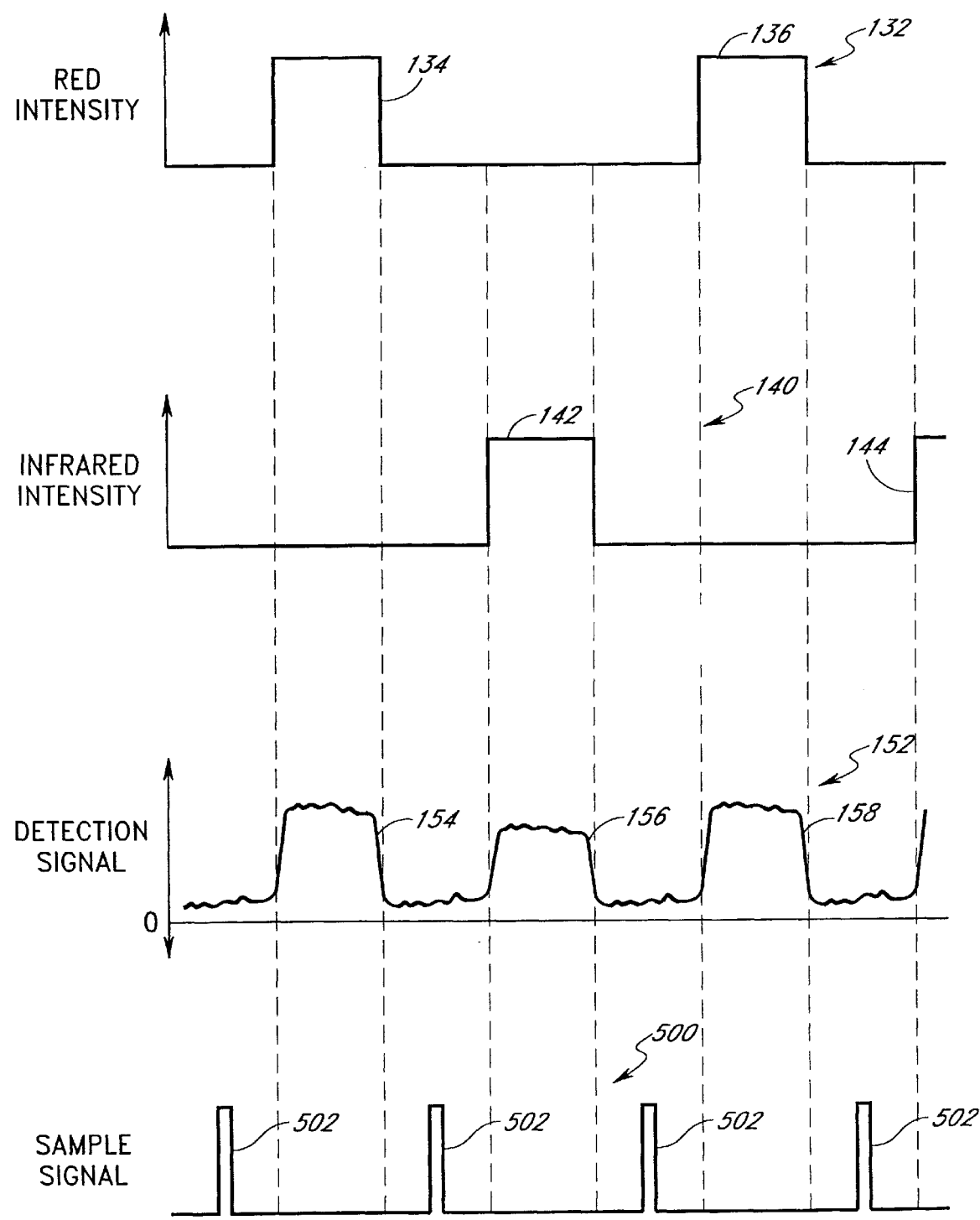
FIG. 12 illustrates a method of time domain sampling the digital detection signal during the times when both the red pulses and the infrared pulses are off to obtain information regarding the level of ambient noise.
Figure 13:
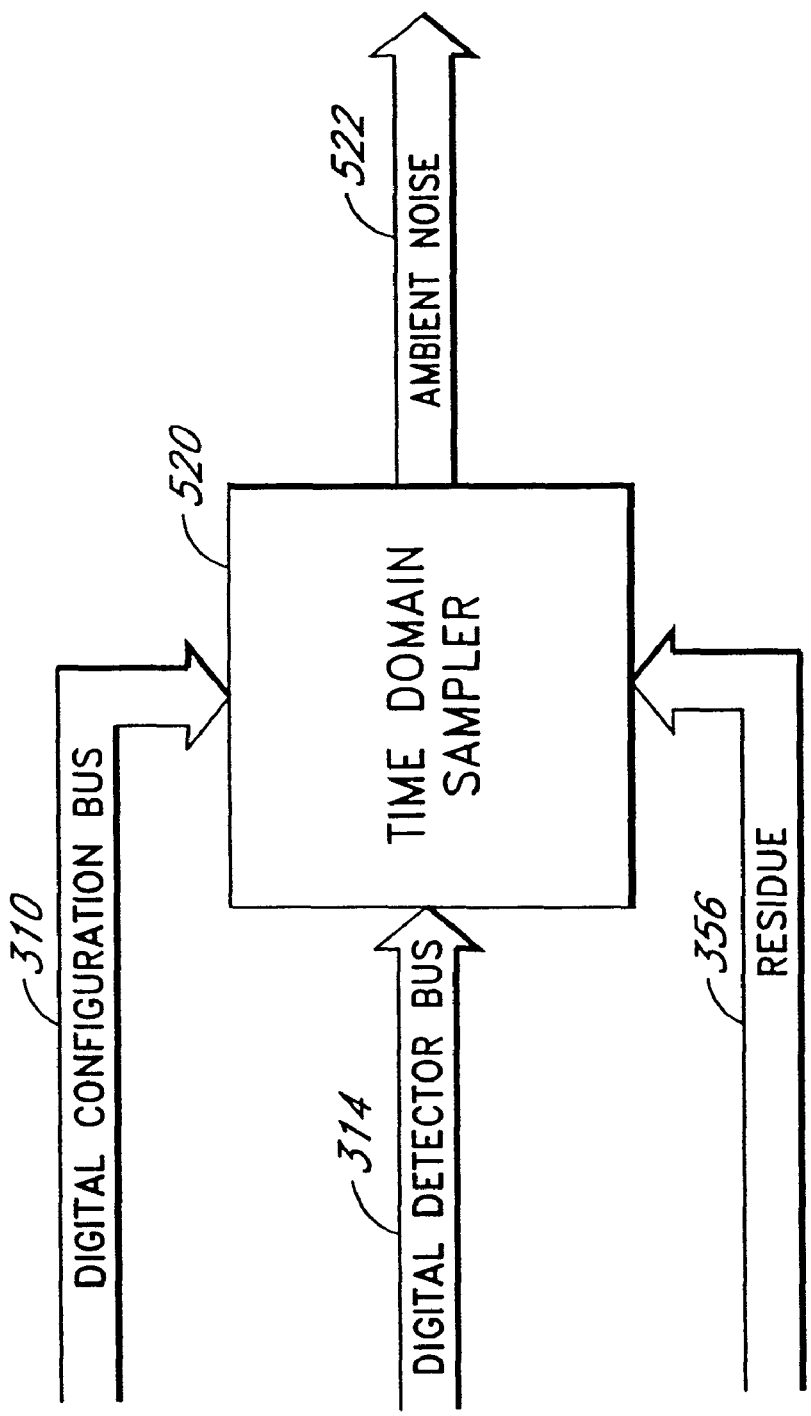
FIG. 13 illustrates a block diagram of a system that performs the time domain sampling of FIG. 12.

Additional information can advantageously be derived from the digitized detection signal on the bus 314 and can be used to provide indications regarding the reliability of the demodulated signals generated as described above. In particular, although the present system is capable of demodulating the $\hat{S}_1(t)$ signal and the $\hat{S}_2(t)$ signal in the presence of significant ambient noise from light and other sources, it is possible that the level of the ambient noise is sufficiently high to affect the demodulated signals. FIGS. 12 and 13 illustrate a time domain method and system for determining the ambient noise level, and FIGS. 14 and 15 illustrate a frequency domain method and system for determining the ambient noise level.

As illustrated in FIG. 12, the digital detection signal 152 is sampled by a sample signal represented by a waveform 500, which comprises a plurality of sampling pulses 502. The sampling pulses 502 are timed to occur during the intervals between the red pulses 134, 136 and the infrared pulses 142, 144 when no red light and no infrared light should be detected by the detector 150 (FIG. 1). Thus, any energy detected during the sample intervals is primarily caused by ambient light and other noise sources. As illustrated, the sampling pulses 502 preferably occur at the approximate midpoint of each interval between the red and infrared pulses.

As illustrated in FIG. 13, the digital detection signal bus 314 is provided as an input to a time domain sampler 520. The time domain sampler 520 also receives the RESIDUE signal on the bus 356 as a second input. The time domain sampler is responsive to the RESIDUE signal to sample the digital detection signal at times when the value of the RESIDUE signal corresponds to the quiescent times of the red pulses 134, 136 and the infrared pulses 142, 144. As described above, the red pulses 134, 136 are generated when the RESIDUE signal has values between 0 and 36, and the infrared pulses are generated when the RESIDUE signal has values between 74 and 110. Thus, assuming no hardware delay, the sampling pulses 502 are preferably generated, for example, when the RESIDUE signal has a value of 55 and when the RESIDUE signal has a value of 129, which positions the sampling pulses at the approximate midpoints of the quiescent intervals between the pulses. As discussed above, the actual system has a hardware delay caused by processing times. Thus, if the system has a hardware delay factor of, for example, 39, the sampling pulses 502 are shifted in time to occur when the RESIDUE signal has a value of 94 and a value of 20 (168 $modulo_{148}$). The sample times used by the time domain sampler 520 are advantageously determined by configuration signals received via the digital configuration bus 310, described above. For example, the time domain sampler 520 can be initially set to sample at RESIDUE signal values of 55 and 129, and the value of the hardware delay value factor (HWΔ) communicated by the digital configuration bus 310 is added to both values to shift the sample to the correct sample interval.

Figure 14:
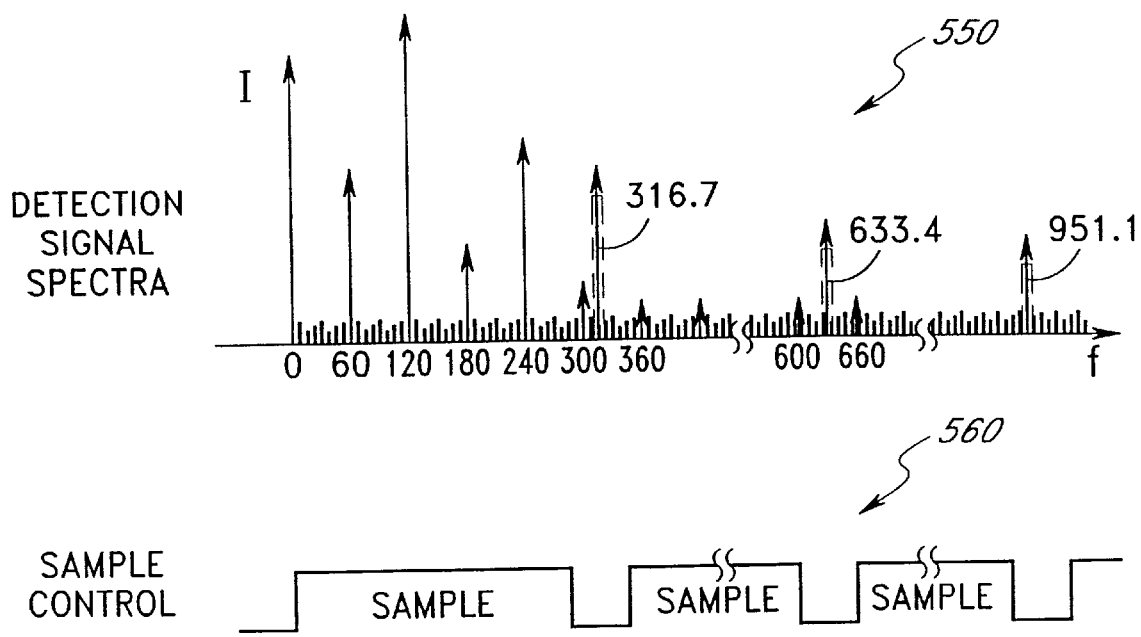
FIG. 14 illustrates a method of frequency domain sampling to determine the noise floor at frequencies other than the signal frequencies.
Figure 15:
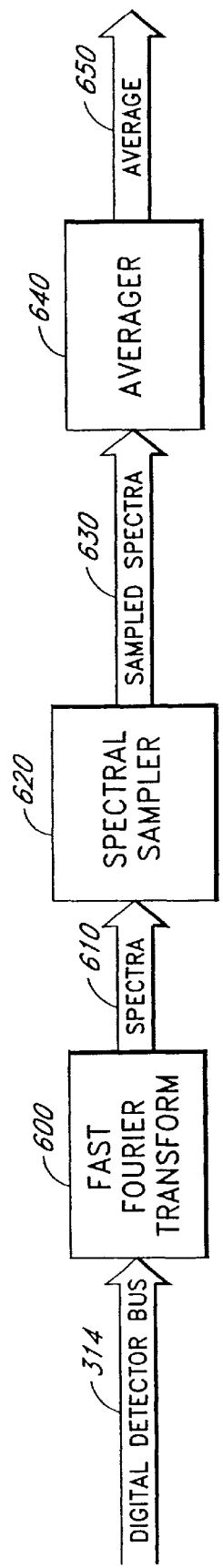
FIG. 15 illustrates a block diagram of a system that performs the frequency domain sampling of FIG. 14.

As illustrated in FIG. 14, a detection signal spectra 550 includes the two frequency components corresponding to the fundamental and first harmonic of the modulation signal at 316.7 Hz and 633.4 Hz, respectively. The spectra 550 further includes the fundamental and multiple harmonics of the 60 Hz power line frequency. In addition, the spectra 550 includes noise at a multitude of frequencies which may be caused by various sources. One particularly troublesome source of noise encountered in pulse oximetry systems is an electrocauterization device, which uses a high frequency electrical current to make surgical incisions and to cauterize the surrounding blood vessels at the same time. Although primarily high frequency noise sources, such devices also generate significant noise at lower frequencies because of arcing. When an electrocauterization device is operated close to a pulse oximeter detector, the noise generated by the device can overwhelm the signals generated by the pulse oximetry detector. In other words, the noise floor can be greater than the detectable signal from the pulse oximetry detector.

It is desirable to detect when the noise floor is too high so that the pulse oximetry system can indicate that the demodulated signals may not be reliable. In order to determine the level of the noise floor, the present invention samples the spectra 550 to determine the content of the frequency components detected at frequencies other than the fundamental and harmonic frequencies of the modulation signals. In particular, as illustrated by a sample control signal 560 in FIG. 14, the portions of the spectra 550 which do not include the fundamental and harmonics of the modulation signal are sampled. Thus, in the preferred embodiment, the magnitudes of the spectra at 316.7 Hz, 633.4 Hz, 950.1 Hz, etc., are not sampled. Furthermore, because a band of frequencies around the fundamental and harmonics of the modulation signal also include significant information caused by the modulation of the red pulses and the infrared pulses by the changes in blood flow during each cardiac cycle. Thus, as illustrated in FIG. 14, in the preferred embodiment, a band of frequencies surrounding the fundamental and harmonic frequencies of the modulation signals (i.e., the sidebands discussed above) are not included in the samples. For example, a band of at least ±10 Hz around each of the fundamental and harmonic frequencies is not included in the samples.

The intensities at the sampled frequencies are averaged, and an output signal is generated which represents the average intensity of the noise signals. Other portions (not shown) of the digital processing system advantageously monitor the average intensity of the noise signals, and, if the average intensity exceeds a selected threshold based upon the size of the measured plethysmograph, then the demodulated output signals from the system are considered as being unreliable and should not be used.

FIG. 15 illustrates a preferred embodiment of a system that determines the noise floor, as described above. The system of FIG. 15 includes a Fast Fourier Transform block 600 which receives a plurality of samples from the digitized detector bus 314 and generates a transformed output on a bus 610. The transformed output on the bus 610 represents the spectra of the samples. In the preferred embodiment, a sufficient number of samples are taken to represent approximately 44 milliseconds of data so that at least two cycles of the 60 Hz power are included within the samples. For example, approximately 1,024 samples can be taken during the 44-millisecond interval at a sample rate of approximately 23.4 kHz (e.g., one-half the system timing rate). The spectra for a 44-millisecond interval are provided as inputs to a spectral sampler 620 which eliminates the samples in the ±10 Hz bands around the fundamental and harmonic frequencies of the modulation signals. The output of the spectral sampler 620 is provided on a bus 630 and is thereby provided as an input to an averager 640. The averager 640 averages the sampled noise spectra which it receives and provides an averaged output on a bus 650. The averaged output on the bus 650 represents the noise floor and is provided to other portions of the digital processing system where it is compared to the selected threshold to determine whether the noise floor is excessive. The threshold is not necessarily fixed, but is dependent on the strength of the plethysmograph, which in turn depends upon the perfusion of blood in the body portion being measured.

The embodiment of FIG. 15 can also advantageously be used to determine whether the ambient noise is primarily at 60 Hz, corresponding to power line frequencies in the United States and Canada, or at 50 Hz, corresponding to power line frequencies in Europe. The foregoing modulation frequency of 316.7 Hz is selected to avoid the harmonics of the 60 Hz power line frequency as well as the 50 Hz power line frequency. If a significant shift in the power line frequency is detected such that aliasing of the ambient noise occurs at the frequencies of interest, then the modulation frequency can be changed to displace the modulation harmonics farther from the harmonics of the power line frequency, such as, for example, by changing the 46,875 Hz sampling frequency, or by changing the modulus.

Pre-Demodulation Decimation

For convenience, the previous embodiments do not show the signal MF(k) being decimated before demodulation. However, as discussed in more detail below, the signal MF(k) can advantageously be decimated prior to demodulation. The pre-demodulation decimation technique can reduce the computational burden required to perform the demodulation operations, primarily because the decimated sample rate is lower than the original (undecimated) sample rate. Computation can also be reduced because, as will be seen, the numerical sequences used in the demodulator are, in some circumstances, shorter than the sequences given in Equations 32 and 33. Pre-demodulation decimation is a generalization of the previous embodiments and reduces to the previous embodiments when the pre-demodulation decimation rate is one.

Figure 16:
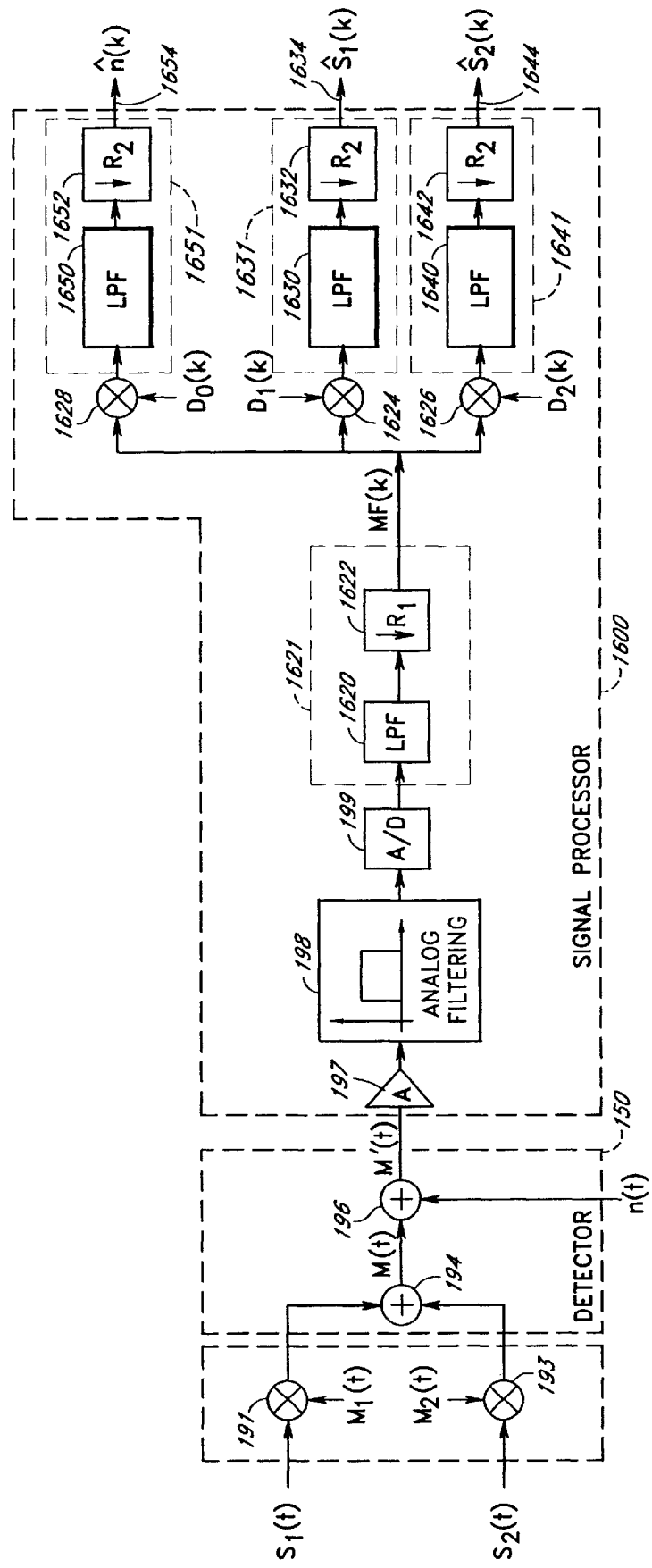
FIG. 16 illustrates a block diagram of the overall processing system in accordance with a pre-demodulation decimation embodiment of the present invention.

FIG. 16 is a pictorial representation of a system that incorporates pre-demodulation filtering and decimation. FIG. 16 is similar to FIG. 3, and like numbers refer to like elements in the two figures. FIG. 16 shows the first modulator 191 having a signal input $S_1(t)$ and a modulation input $M_1(t)$. The second modulator 193 has a signal input $S_2(t)$ and a modulation input $M_2(t)$. The pair of signals $S_1(t)$ and $S_2(t)$ represent the effect of the time-varying volume and scattering components of the blood in a finger (or other body part) on the red light and the infrared light, respectively, passing through the finger. The red light signal portion $S_1(t)$ is caused by the variable attenuation of the red light passing through the finger 102 (shown in FIG. 1). The infrared light signal portion $S_2(t)$ is caused by the variable attenuation of the infrared light passing through the finger 102. The outputs of the first and second modulators 191, 193 are provided to the receiving photodetector 150. The photodetector 150 is modeled as an adder 194 and an adder 196. The outputs of the first and second modulators 191, 193 are provided to the adder 194 to generate a composite signal M(t) where:

$$M(t)=S_1(t)M_1(t)+S_2(t)M_2(t). \tag{34}$$

The output signal M(t) from the adder 194 is provided to an adder 196 where a signal n(t) is added to the signal M(t). The signal n(t) represents a composite noise signal caused by ambient light (including DC and harmonics of the power line frequency), electromagnetic pickup, and the like, which are also detected by the photodetector 150. In addition, the signal n(t) may also include noise at higher frequencies caused, for example, by other devices such as electrocauterization equipment, or the like. The output of the adder 196 is a signal M'(t)=M(t)+n(t) which includes noise components as well as the signal components.

The M'(t) signal output of the adder 196 (i.e., the output of the detector 150) is applied to the input of a signal processing block 1600. Within the signal processing block 1600, the signal M'(t) is first passed through the amplifier 197 and then through the analog bandpass filter 198. The analog bandpass filter 198 provides anti-aliasing and removal of low frequency noise and DC. The filter 198 has a passband selected to pass signals in the preferred range of 20 Hz to 10,000 Hz. The analog bandpass filter 198 removes a significant portion of the noise below 20 Hz. The signal components responsive to the blood oxygen saturation are frequency shifted by the operation of the two modulation signals $M_1(t)$ and $M_2(t)$ and are passed by the analog bandpass filter 198.

In one embodiment, the output of the analog bandpass filter 198 is sampled by the analog-to-digital converter 199 and converted therein to digital signals. In one embodiment, the signals are sampled at 46,875 samples per second. The digital signals from the analog-to-digital converter 199 are provided as inputs to a lowpass digital filter 1620. Output signals from the digital filter 1620 are provided to a sample rate compression block 1622 that reduces (compresses) the sample rate by a decimation rate $R_1$. The lowpass digital filter 1620 and sample rate compressor 1622 together comprise a decimator 1621 (decimation comprises lowpass filtering followed by sample rate compression). The digital filter 1620 provides anti-aliasing filtering and the sample rate compression block 1622 preferably operates at a sampling rate of at least twice the highest frequency of interest as determined by the digital filter 1620. In one embodiment, the sample rate compression block 1622 reduces the sample rate by a factor of $R_1=37$, corresponding to the number of samples during the period $\tau$ as illustrated in FIG. 10. The output of the sample rate compression block 1622 provides one sample per time period $\tau$ and thus four samples per time period T. The output of the sample rate compression block 1622 is a signal MF(k) (where k is a discrete index) which comprises approximately 1,266 samples per second.

The signal MF(k) is provided as a first input to a first mixer 1624. The signal MF(k) is also provided as a first input to a second mixer 1626. A first demodulating signal $D_1(k)$ is provided as a second input to the first mixer 1624, and a second demodulating signal $D_2(k)$ is provided as a second input to the second mixer 1626. The output of the first mixer 1624 is provided as an input to a first lowpass filter 1630, and the output of the second mixer is provided as an input to a second lowpass filter 1640. The bandwidths of the lowpass filters 1630, 1640 are preferably approximately 10 Hz. The signal MF(k) is also provided as a first input to a noise channel mixer 1628. A noise demodulating signal $D_0(k)$ is provided as a second input to the noise channel mixer 1628. The output of the noise channel mixer 1628 is provided to an input of a low pass filter 1650. The output of the low pass filter 1650 is provided to a sample rate compression block 1652. The output of the sample rate compression block 1652 is an estimate of the noise n(t). The output of the lowpass filters 1630 is provided to an input of a sample rate compressor 1632 and the output of the lowpass filter 1640 is provided to an input of a sample rate compressor 1642. The lowpass filter 1630 and the sample rate compressor 1632 together comprise a decimator 1631. The lowpass filter 1640 and the sample rate compressor 1642 together comprise a decimator 1641.

The output of the decimator 1631 is a signal $\hat{S}_1(k)$, which, as discussed below, is an estimate of the signal $S_1(k)$. The output of the decimator 1641 is a signal $\hat{S}_2(k)$, which, as discussed below, is an estimate of the signal $S_2(k)$. As will be shown below, the selection of the first demodulating signal $D_1(k)$ and the second demodulating signal $D_2(k)$ in accordance with the present invention can reduce or eliminate the effects of noise in the two output signals $\hat{S}_1(k)$ and $\hat{S}_2(k)$ and also reduce or eliminate crosstalk between the two signals.

The decimators 1632, 1642 decimate by a decimation rate $R_2$. In a preferred embodiment, the decimators 1632, 1642 decimate by a decimation rate R2=20 to a sample rate of, for example, 63.3 Hz to provide a decimated output which can be further processed in accordance with the methods and apparatuses described in the above-referenced patents. The decimations which occur in the decimators 1632, 1642 reduce the rate at which the output signals $\hat{S}_1(k)$ and $\hat{S}_2(k)$ need to be processed while maintaining the sample rate well above the 10 Hz frequency content of the signals of interest. The outputs of the decimators 1632, 1642 are provided on respective output lines 1634 and 1644.

Decimating the signal MF(k) prior to demodulation, although not an approximation technique, can be simplified by assuming that each desired signal $S_i(t)$ does not change appreciably during each period $\tau$. In many applications it is reasonable to assume that the desired signals $S_1(t)$ and $S_2(t)$ will not change significantly during the time interval $\tau$ shown in FIG. 2. One skilled in the art will recognize that a sufficient condition for this assumption is that the highest significant frequency components in $S_1(t)$ and $S_2(t)$ are much lower than the modulation frequency. In the pulse-oximetry application the highest frequency of interest is typically around 10 Hz, which is far below the 316.7 Hz fundamental of the modulation. Since n(t) is not a desired signal, no such assumption is necessary for n(t). Thus, while n(t) may vary erratically over a modulation cycle, the signals $S_1(t)$ and $S_2(t)$ do not. Therefore, it is possible to perform pre-demodulation decimation that has little effect on $S_1(t)$ and $S_2(t)$ but may shape n(t) into n'(t). The measured signal is decimated by a factor $R_1=Q$ (where Q is the number of samples in a time period $\tau$) and then demodulated.

Assuming $R_1=Q$, then the spectral domain representation of the signal MF(k) at the output of the sample rate compression block 1622 is given by (approximately):

$$MF(f) = \frac{1}{T}\sum_{n=-\infty}^{\infty}\left[S_1\left(f-\frac{n}{T}\right)+(-1)^n S_2\left(f-\frac{n}{T}\right)\right]+ \qquad (35)$$

$$\frac{4}{T}\sum_{m=-\infty}^{\infty} n'\left(f-\frac{4m}{T}\right)$$

Since the sample rate compression block 1622 decimates at the same rate as the number of samples per period $\tau$, the decimation removes any $\tau$ dependence in the expression for MF(f). The frequency components indexed by m increase four times faster than the frequency components indexed by n. This occurs because the modulated signals $S_1(t)$ and $S_2(t)$, which are indexed by n, occur in only one fourth of the samples, but the noise n(t), which is indexed by m, occurs in every sample.

The demodulation operation can be performed either in the frequency or the time domain. A method for frequency domain demodulation of the signal MF(k) can be obtained by rewriting Equation 35 as:

$$MF(f)= \ldots MF_{-2}(f)+MF_{-1}(f)+MF_0(f)+MF_1(f)+MF_2(f)+\ldots \quad (36)$$

where $$MF_{-2}(f)=[S_1(f)+S_2(f)]/T$$

$$MF_{-1}(f)=[S_1(f)-S_2(f)]/T$$

$$MF_0(f)=[S_1(f)+S_2(f)+4n'(f)]/T$$

$$MF_1(f)=[S_1(f)-S_2(f)]/T$$

$$MF_2(f)=[S_1(f)+S_2(f)]/T$$

$$MF_3(f)=[S_1(f)-S_2(f)]/T$$

$$MF_4(f)=[S_1(f)+S_2(f)+4n'(f)]/T \qquad (37)$$

Where n'(k) is the decimated noise signal n(t). Estimates for the signal $S_1(f)$ can be obtained by shifting the spectra of $MF_1(f)$ and $MF_2(f)$ by $-1/T$ and $-2/T$, respectively, and then dividing the sum of the resultant by 2. Likewise, $S_2(f)$ can be obtained by dividing the difference of the resultant spectra by 2. In other words:

$$\hat{S}_1(f)=MF_1(f-1/T)+MF_2(f-2/T)$$

$$\hat{S}_2(f)=MF_1(f-1/T)-MF_2(f-2/T) \qquad (38)$$

Demodulation in the time domain is a more elegant method for obtaining $S_1(k)$ and $S_2(k)$. Time domain demodulation is obtained by using the frequency shift property of the Fourier transform given by:

$$F(\omega+\omega_0) \Leftrightarrow e^{-j\omega_0 t}f(t) \qquad (39)$$

According to Equation 39, the frequency domain terms $MF_i(f)$ are related by a time shift in the time domain and this property can be used to generate the demodulation sequences $D_0$–$D_2$. A more complete development of this process (for the general case of N channels) is provided in Equations 42–50 below and in the text accompanying those equations. For the present case, where N=2, using equations 42–50 gives:

$$D_0(k) = 0,1,0,1, \ldots$$

$$D_1(k) = 1,-0.5,0,-0.5, \ldots$$

$$D_2(k) = 0,-0.5,1,-0.5, \ldots \qquad (40)$$

The sequences shown in Equation 40 are repeating sequences of the four values shown. Thus, the demodulation waveforms are no more than short repeating sequences of simple coefficients. Since the samples MF(k) are time domain sequences, demodulation simply involves multiplying the samples MF(k) by the sequences in Equation 40. For example, the sequence of coefficients $D_0(k) = (0, 1, 0, 1, \ldots)$ is provided to the multiplier 1628 to demodulate the signal MF(k) and produce the estimate of n(k). Similarly, the sequence of coefficients $D_1(k) = (1, -0.5, 0, -0.5, \ldots)$ is provided to the multiplier 1624 to demodulate the signal MF(k) and produce the estimate of $S_1(k)$.

Multiple Channel Modulation and Demodulation

Figure 17:
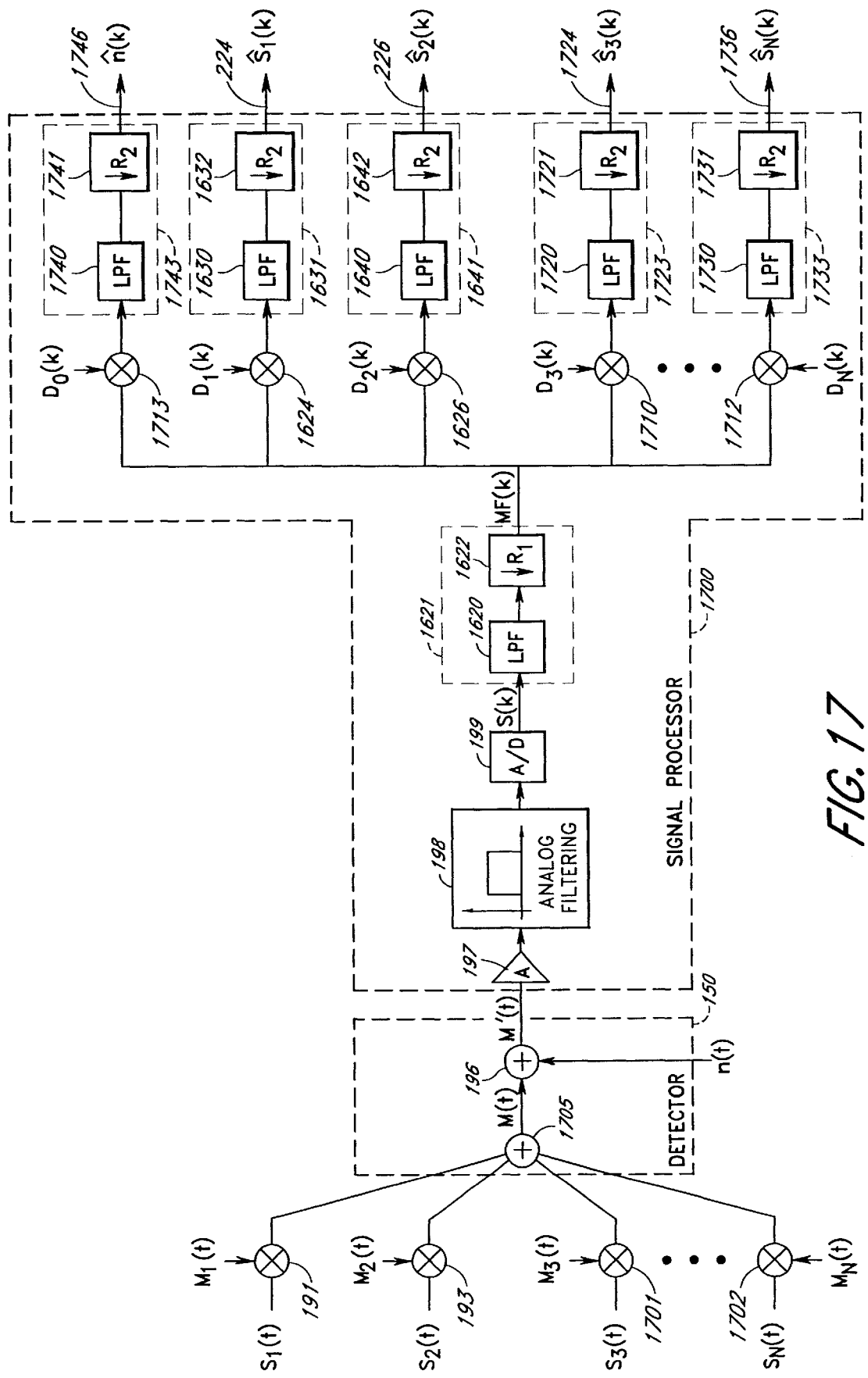
FIG. 17 illustrates a block diagram of a multi-channel processing system in accordance with a pre-demodulation decimation embodiment of the present invention.

The two-channel pre-demodulation decimation technique described in the previous section can be extended to multi-channel systems having more than two desired signals. FIG. 17 illustrates an expansion of the two-channel modulator into a multi-channel modulator/demodulator. FIG. 17 shows the first modulator 191 and the second modulator 193 as shown in FIG. 16. Further, FIG. 17 shows a third modulator 1701 and an $N^{th}$ modulator 1702. The signal input $S_1(t)$ and a modulation input $M_1(t)$ are provided to the first modulator 191. The signal input $S_2(t)$ and a modulation input $M_2(t)$ are provided to the second modulator 193. A signal input $S_3(t)$ and a modulation input $M_3(t)$ are provided to the third modulator 1701. A signal input $S_N(t)$ and a modulation input $M_N(t)$ are provided to the $N^{th}$ modulator 1702.

The photodetector 150 is modeled as an adder 194 and an adder 196. The outputs of the modulators 191, 193, 1701, and 1703 are added together in the adder 194, to generate a composite signal M(t) where:

$$M(t) = S_1(t)M_1(t) + S_2(t)M_2(t) + S_3(t)M_3(t) + \ldots + S_N(t)M_N(t) \qquad (41)$$

The signal M(t) from the adder 194 is provided to the adder 196 where the signal M(t) is added to the signal n(t) which represents a composite noise signal caused by ambient light, electromagnetic pickup, and the like, which are also detected by the photodetector 150. The output of the adder 196 is the signal M'(t)=M(t)+n(t), which includes the noise components as well as the signal components.

The M'(t) signal output of the adder 196 (i.e., the output of the detector 150) is applied to the input of the signal-processing block 1700. Within the signal-processing block 1700, the signal M'(t) is first passed through an amplifier 197 and then through the analog bandpass filter 198. The analog bandpass filter 198 provides anti-aliasing and removal of low frequency noise and DC. The desired signal components in the signals $S_i(t)$ are frequency shifted by the operation of the modulation signals $M_i(t)$ and are passed by the analog bandpass filter 198.

The output of the analog bandpass filter 198 is sampled by the analog-to-digital converter 199 and converted therein to digital signals and provided to an input of the lowpass digital filter 1620. Output signals from the digital filter 1620 are provided to a sample rate compression block 1622, which reduces the sample rate by a decimation factor $R_1$. Together, the digital filter 1620 and the sample rate compression block 1622 comprise a decimator 1621. The output of the sample rate compression block 1622 is a signal MF(k). The signal MF(k) is provided as: the first input to the first mixer 1624; the first input to the second mixer 1626; a first input to a third mixer 1710; a first input to an N'th mixer 1712; and a first input to a noise channel mixer 1713. A first demodulating signal $D_1(k)$ is provided as a second input to the first mixer 1624. A second demodulating signal $D_2(k)$ is provided as a second input to the second mixer 1626. A third demodulating signal $D_3(k)$ is provided to the third mixer 1710. A fourth demodulating signal $D_N(k)$ is provided to the $N^{th}$ mixer 1712. A noise demodulating signal $D_0(k)$ is provided to the noise channel mixer 1713. The outputs of the mixers 1624, 1626, 1710, 1712, and 1713 are provided as respective inputs of the lowpass filters 1630, 1640, 1720, 1730, and 1740. The outputs of the lowpass filters 1630, 1640, 1720, 1730, and 1740 are provided as respective inputs of the decimators 1632, 1642, 1721, 1731 and 1741. Each of the decimators 1632, 1642, 1721, 1731 and 1741 reduces the sample rate by a decimation rate $R_2$.

The output of the sample rate compressor 1632 is a signal $\hat{S}_1(k)$, which, as discussed below, is an estimate of the signal $S_1(k)$. Likewise, the output of the sample rate compressor 1642 is an estimate of $S_2(t)$, the output of the sample rate compressor 1721 is an estimate of the signal $S_3(t)$, the output of the sample rate compressor 1731 is an estimate of the signal $S_N(t)$, and the output of the sample rate compressor 1741 is an estimate of the signal n(t).

As will be shown below, the selection of the demodulating signals $D_i(t)$ for $i=0 \ldots N$ in accordance with the present invention can substantially reduce or eliminate the effects of noise in the output signals $\hat{S}_i(k)$ and n(k), and can also substantially reduce or eliminate crosstalk between the signals.

As shown in FIG. 17, a set of N+1 signals $S_i[k]$ i=1 . . . N, and n(k) are sampled at a rate T/QN, where T is a modulation period. For simplicity, the decimation rate $R_1$ is assumed to be the same as the factor Q. The assumption that $R_1$=Q is not a necessary assumption, but rather is used here to simplify the mathematics. The signals are combined according to the formula:

$$S(k) = M_1(k)S_1(k) + M_2(k)S_2(k) + M_3(k)S_3(k) + \ldots + M_N(k)S_N(k) + n(k) \qquad (42)$$

Using the symbol * to denote the convolution operator, the terms $M_i(k)$ are given by:

$$M_1(k) = \Delta(2Nt/T) * P_1(t)|_{t=kT/QN}$$

$$M_2(k) = \Delta(2Nt/T) * P_2(t)|_{t=kT/QN}$$

$$M_N(k) = \Delta(2Nt/T) * P_N(t)|_{t=kT/QN} \qquad (43)$$

where $$\Delta(x) = \begin{cases} 1 & \text{if } |x| \leq 0.5 \\ 0 & \text{otherwise} \end{cases} \qquad (44)$$

and $$P_1(t) = \sum_{n=-\infty}^{\infty} \delta(t - nT) \qquad (45)$$

(where $\delta(k)$ is the Kröneker delta function, which is 1 for k=0, and 0 for all other values of k), and $$P_i(t) = P_1\left(t - \frac{(i-1)T}{N}\right) \text{ for } i = 2 \ldots N \qquad (46)$$

After the pre-demodulation and sample rate compression stage 1622, which decimates by a factor Q, the signal in the frequency domain is given approximately by $$MF(f) = \qquad (47)$$

$$\frac{1}{T}\sum_{n=-\infty}^{\infty}\left|S_1\left(f-\frac{n}{T}\right) + \xi_1^n S_2\left(f-\frac{2n}{T}\right) + \ldots + \xi_{N-1}^n S_N\left(f-\frac{Nn}{T}\right)\right| +$$

$$\frac{2N}{T}\sum_{m=-\infty}^{\infty} S_n\left(f-\frac{2Nm}{T}\right)$$

where $$\xi_k^n = e^{\frac{j2\pi kn}{N}}$$

The demodulator sequences are then given by:

$$D_0(k) = \frac{(1-(-1)^k)}{2} \qquad (49)$$

$$D_1(k) = P_1(k) - \frac{D_0(k)}{N}$$

$$D_2(k) = P_2(k) - \frac{D_0(k)}{N}$$

. 
.
.

$$D_N(k) = P_N(k) - \frac{D_0(k)}{N}$$

where $$P_1(k) = P_1(t)|_{t=\frac{kT}{2N}}, \quad P_2(k) = P_2(t)|_{t=\frac{kT}{2N}}, \quad \ldots, \qquad (50)$$

$$P_N(k) = P_N(t)|_{t=\frac{kT}{2N}}$$

The post demodulation lowpass filters 1630, 1640, 1720, 1730 and 1740, and the post demodulation sample rate compression stages 1632, 1642, 1721, 1731 and 1741 suppress high frequency artifacts which are produced by the modulation/demodulation process. Note that Equation 49 reduces to Equation 40 for N=2.

Adaptive Demodulation

Figure 18:
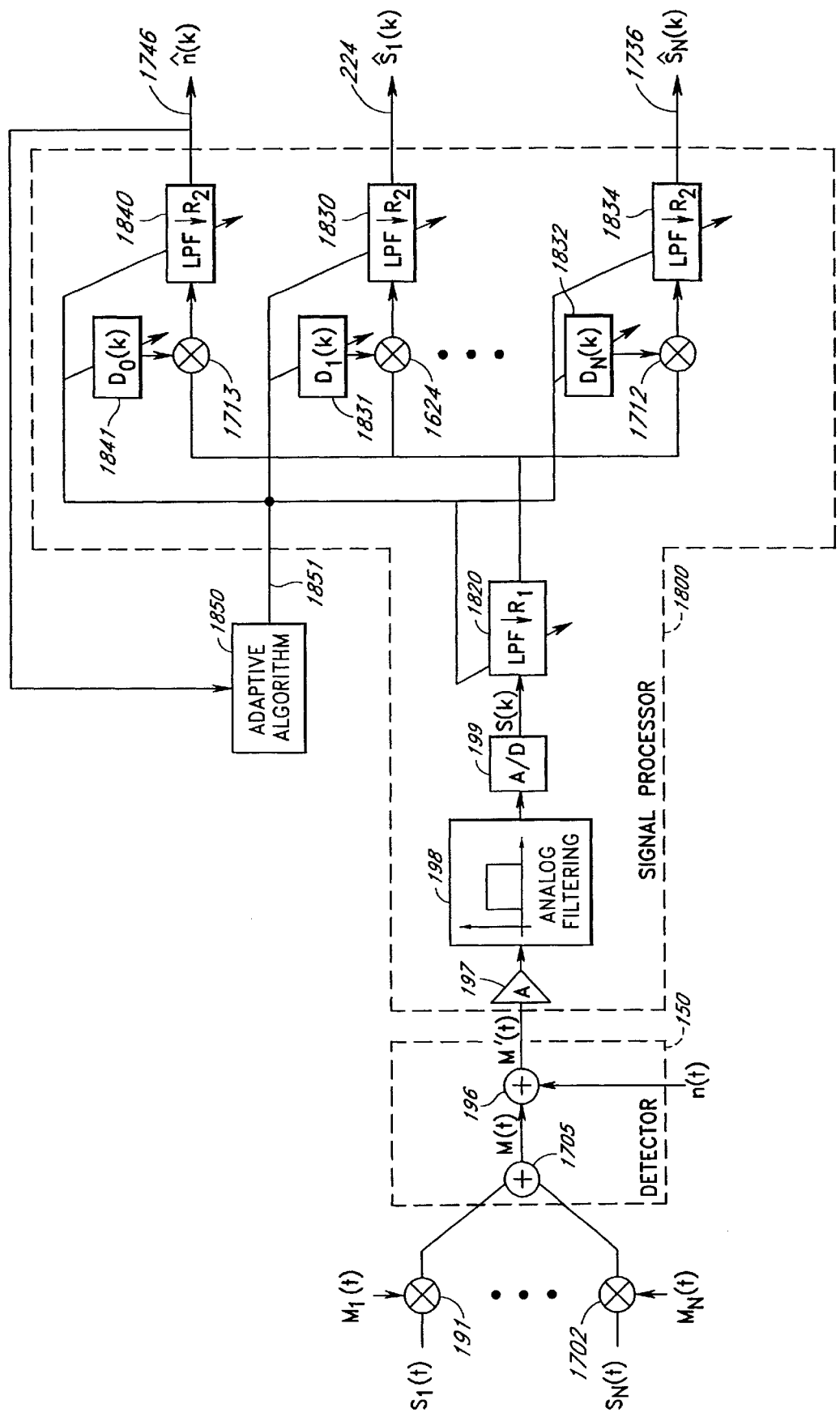
FIG. 18 illustrates a block diagram of an adaptive multi-channel processing system in accordance with a pre-demodulation decimation embodiment of the present invention.

The multi-channel pre-demodulation decimation technique described in the previous section can be extended to an adaptive multi-channel system having an adjustable pre-demodulation decimation rate and an adjustable post-demodulation decimation rate. FIG. 18 illustrates an expansion of the multi-channel modulator into a adaptive multi-channel modulator/demodulator 1800. FIG. 18 shows the first modulator 191 and the N$^{th}$ modulator 1702 as shown in FIG. 17. The signal input $S_1(t)$ and a modulation input $M_1(t)$ are provided to the first modulator 191. A signal input $S_N(t)$ and a modulation input $M_N(t)$ are provided to the N$^{th}$ modulator 1702.

The photodetector 150 is modeled as an adder 194 and an adder 196. The outputs of the modulators 191, 193, 1701, and 1703 are added together in the adder 194, to generate a composite signal M(t) where:

$$M(t) = S_1(t)M_1(t) + \ldots + S_N(t)M_N(t) \qquad (51)$$

The signal M(t) from the adder 194 is provided to the adder 196 where the signal M(t) is added to the signal n(t) which represents a composite noise signal caused by ambient light, electromagnetic pickup, and the like, which are also detected by the photodetector 150. The output of the adder 196 is the signal M'(t)=M(t)+n(t), which includes noise components as well as the signal components.

The M'(t) signal output of the adder 196 (i.e., the output of the detector 150) is applied to the input of the signal-processing block 1800. Within the signal-processing block 1800, the signal M'(t) is first passed through the amplifier 197 and then through the analog bandpass filter 198. The analog bandpass filter 198 provides anti-aliasing and removal of low frequency noise and DC. The desired signal components in the signals $S_i(t)$ are frequency shifted by the operation of the modulation signals $M_i(t)$ and are passed by the analog bandpass filter 198.

The output of the analog bandpass filter 198 is sampled by the analog-to-digital converter 199 and converted therein to digital signals and provided to an input of a decimation block 1820. The adaptive decimation block 1820 comprises a digital lowpass filter and a sample rate compressor that reduces the sample rate by the decimation rate $R_1$. The filter coefficients and decimation rate $R_1$ are provided to a control input of the adaptive decimation block 1820 by an output of an adaptive algorithm block 1850. Equation 35 assumes that the decimation rate $R_1$ is equal to Q. However, in general, the value of Q may be different than the decimation rate $R_1$. The output of the adaptive decimation block 1820 is a signal MF(k).

The signal MF(k) is provided to the first input of the first mixer 1624, to the first input of the N'th mixer 1712, and to the first input of the noise channel mixer 1713. A first demodulating signal $D_1(k)$ is provided to a second input of the first mixer 1624 from a signal generator 1841. The fourth demodulating signal $D_N(k)$ is provided to the N$^{th}$ mixer 1712 from an output of a signal generator 1831. The noise demodulating signal $D_0(k)$ is provided to the noise channel mixer 1713 from an output of a signal generator 1832. A control input to each of the signal generators 1831, 1832, and 1841 is provided by the output of the adaptive algorithm 1850. In yet another embodiment, the adaptive algorithm 1850 may also be controlled by other signal processing elements downstream of the signal processor 1800.

The outputs of the mixers 1713, 1624, and 1712 are provided as respective inputs to adaptive decimation blocks 1840, 1830, and 1834 respectively. Each of the adaptive decimation blocks 1840, 1830, and 1834 has a control input provided by the output of the adaptive algorithm block 1850. The output of the adaptive decimation block 1840 is an estimate of the signal n(t) and it is provided to an input of the adaptive algorithm block 1850. In an alternate embodiment, the signal estimates $\hat{S}_i(k)$ are also provided to the adaptive algorithm block 1850.

An output of the decimator 1830 is a signal $\hat{S}_1(k)$, which, as discussed above, is an estimate of the signal $S_1(k)$. Likewise, the output of the decimation block 1834 is an estimate of the signal $S_N(t)$. As shown above, the selection of the demodulating signals $D_i(t)$ for i=0 . . . N in accordance with the present invention substantially reduces or eliminates the effects of noise in the output signals $\hat{S}_i(k)$ and n(k), and also substantially reduces or eliminates crosstalk between the signals.

As shown in FIG. 18, a set of N+1 signals $S_i[k]$ i=1 . . . N, and n(k) are sampled at a rate T/QN, where T is a modulation period, and $R_1$ is the decimation rate of the decimation block 1820. The signals are combined according to the formula:

$$S(k)=M_1(k)S_1(k)+ \ldots +M_N(k)S_N(k)+n(k) \tag{52}$$

Each of the adaptive decimators 1820, 1840, 1830, and 1834 comprises a digital lowpass filter and a sample rate compressor. The characteristics of the digital lowpass filters (e.g., the number of filter coefficients and values of the filter coefficients) and the sample rate compression factor of each adaptive decimator is provided to a control input of the adaptive decimator. The control inputs are driven by an adaptive algorithm 1850. The signal generators 1831, 1832 and 1841 generate the demodulation sequences for the demodulators 1624, 1712, and 1713 respectively. The demodulation sequences produced by the signal generators 1831, 1832 and 1841 are controlled by the adaptive algorithm 1850.

The adaptive algorithm adjusts the pre-demodulation decimation rate $R_1$ (in the adaptive demodulator 1820), and the post-demodulation decimation rate $R_2$ (in the adaptive demodulators 1830, 1834 and 1840) according to the noise in the noise estimate n̂(k) 1746 and (optionally) according to the signals $\hat{S}_r(k)$. The product $R_1R_2$ is the total decimation rate from the signal S(k) at the output of the A/D converter 199 to the signals $\hat{S}_r(k)$ at the output of the signal processing block 1800. The adaptive algorithm may adjust $R_1$ and $R_2$ such that the product $R_1R_2$ varies, or the adaptive algorithm may adjust $R_1$ and $R_2$ such that the product $R_1R_2$ is substantially constant. Typically, the adaptive algorithm will keep the $R_1R_2$ product constant so that the signal processing blocks downstream of the signal processor 1800 will operate at a substantially constant sample rate.

Typically, each of the signal generators 1841, 1831 and 1832 generates a repeating sequence of numbers. The number of elements in the sequence is a function of the decimation factor $R_1$. As discussed above in connection with FIG. 3, when $R_1=1$, there are preferably 148 values in each demodulation sequence. As discussed above in connection with FIG. 17, when $R_1=37$, there are preferably only 4 values in the demodulation sequences.

The adaptive algorithm selects $R_1$, $R_2$, and the filter transfer functions in the adaptive decimators 1820, 1830, 1834, and 1840 to improve the quality of the output signals $\hat{S}_r(k)$. For example, in high ambient noise environments, the higher order harmonics of the output signals are often contaminated by ambient noise (as discussed in connection with FIGS. 14 and 20). Thus, the higher order harmonics are preferably not demodulated when ambient noise is present. To avoid demodulation of the higher order harmonics the adaptive demodulator 1850 can set $R_1=1$ and $R_2=37$, and thereby demodulate according to the method described in connection with FIGS. 3–14. Alternatively, the adaptive demodulator 1850 can set $R_1=37$, set $R_2=1$, and set the transfer function of the lowpass filter in the adaptive decimator 1820 to provide a very fast rolloff (thereby filtering out the higher order harmonics).

Conversely, in low ambient noise environments, the higher order harmonics of the output signal are less contaminated by ambient noise, and thus the higher order harmonics may be demodulated. In one embodiment, to demodulate the higher order harmonics, the adaptive demodulator 1850 can set $R_1=37$ and set $R_2=1$, to demodulate according to the method described in connection with FIG. 17. This is especially advantageous when perfusion is low, because, when perfusion is low the output signals $\hat{S}_r(k)$ are typically very weak and are contaminated by random noise. Demodulating more of the higher order harmonics increases the signal-to-noise ratio because it adds the harmonics (which are correlated) to the output signals, and tends to average out the noise (which is uncorrelated). Thus, the signal strength increases, and the noise is reduced.

One skilled in the art will recognize that the examples in the preceding two paragraphs are merely two points on a continuum and that the adaptive algorithm 1850 can generate many desirable solutions on the continuum.

Ambient Light Rejection

In the pulse oximeter, one of the major contributors to the noise signal n(t) is ambient light that is detected by the photodetector 150. One aspect of the present invention advantageously provides a method for choosing the modulation sampling rate $f_s$ and the factor Q so that the effects of ambient light can be removed by the post demodulation filtering and decimation stages. Note that Q is the number of samples during the on period (i.e., modulation signal sample turn on time Q) and is preferably also the decimation rate $R_1$ for the pre-demodulation sample rate compressor 1622 (in general the values of Q and $R_1$ may be different). The particular embodiment described by Equation 35 assumes that the value Q is also used as decimation rate $R_1$ for the pre-demodulation decimator 1820.

In the system shown in FIGS. 3 and 16, which demodulates two harmonics, the period of a modulation cycle is given by:

$$T=4Q/f_s \tag{53}$$

where $f_s$ is the sample rate. Defining the two line equations $$y(f_a, n) = nf_a - \frac{1}{T} \tag{54}$$

$$z(f_a, n) = nf_a - \frac{2}{T}$$

where $f_a$=line frequencies of concern $n$=line frequency harmonic numbers of concern (55)

then the effects due to ambient light will be minimized when $$|y(f_a,n)| \geq SBF$$

$$|z(f_a,n)| \geq SBF \tag{56}$$

where SBF is the stop band frequency of the post demodulation and decimation stages (e.g., the 10 Hz lowpass filter 1630 and the sample rate compressor 1632, etc.).

Figure 19:
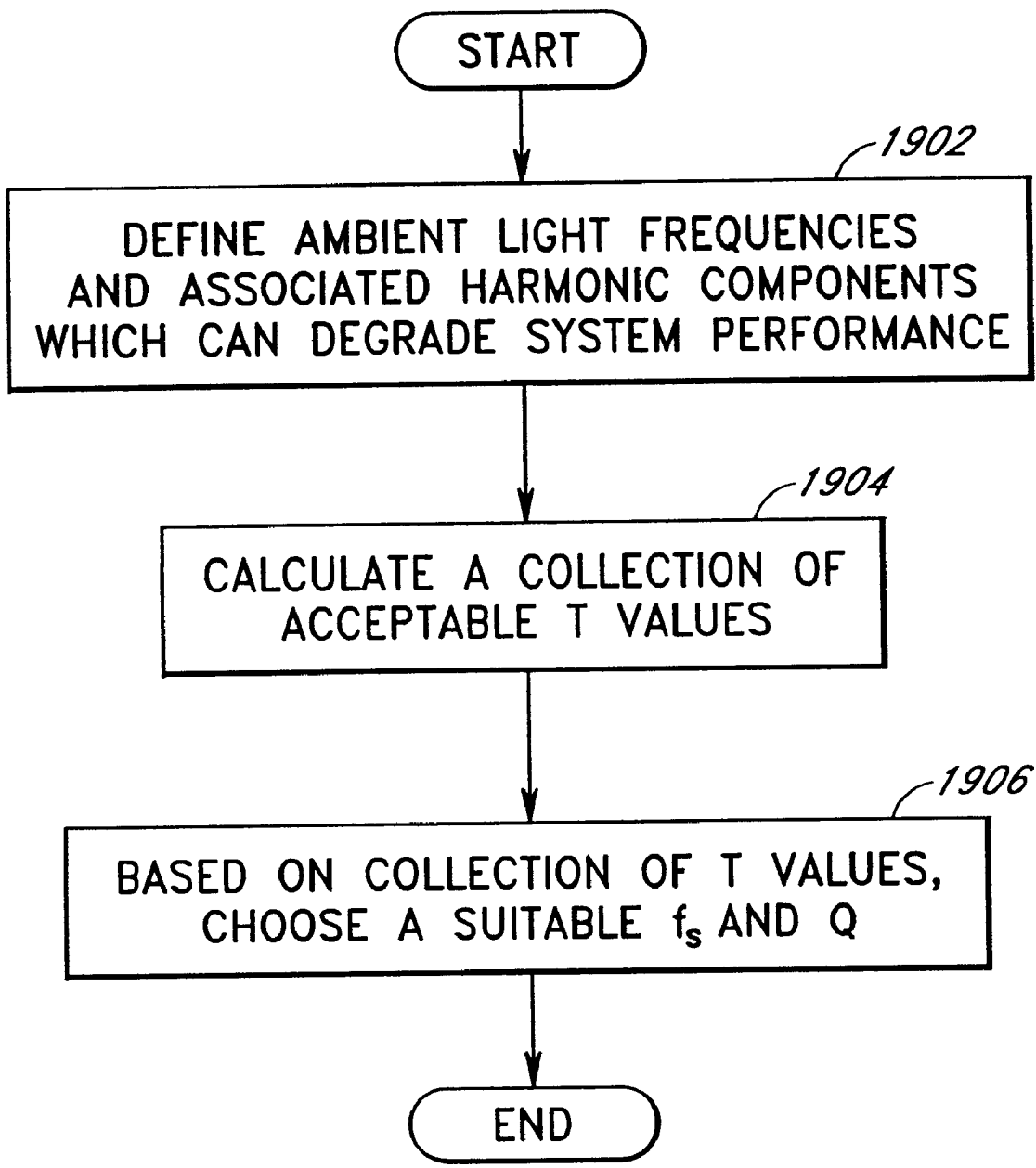
FIG. 19 illustrates a flowchart of a method for choosing the modulation frequency and decimation rate in order to minimize the affects of ambient light.

FIG. 19 is a flowchart showing a method for selecting $f_s$ and Q. The method begins at a process block 1902 wherein the ambient light frequencies $f_a$ and important harmonic components n are identified. Important harmonics are defined as those harmonics that will degrade system performance below acceptable levels when detected by the detector 150. The process then advances from the process block 1902 to a process block 1904. In the process block 1904, the values of $f_a$ and n identified in the process block 1902 are used in conjunction with Equation 54 to identify a collection of acceptable values of T. Upon completion of the process block 1904, the process advances to a process block 1906. In the process 1906, suitable values of $f_s$ and Q are chosen using the values of T obtained in the process block 1904 and the equation $T=4Q/f_s$. One skilled in the art will recognize that, since T is proportional to the ratio of $Q/f_s$, knowing T will not uniquely determine either $f_s$ or Q.

For example, given power line frequencies of 50±1 Hz and 60±1 Hz then the range of $f_a$ is given by approximately the union of the interval 49–51 Hz and the interval 59–61 Hz, which can be expressed mathematically as:

$$f_a \approx [49,51] \cup [59,61] \qquad (57)$$

Assuming that all harmonics up to the 18$^{th}$ harmonic are to be suppressed, then n=1 ... 18. In a preferred embodiment, using these values for $f_a$ and n, application of the method in FIG. 19 results in $f_s$=46,875 Hz and acceptable Q values of 37 and 41.

Figure 20:
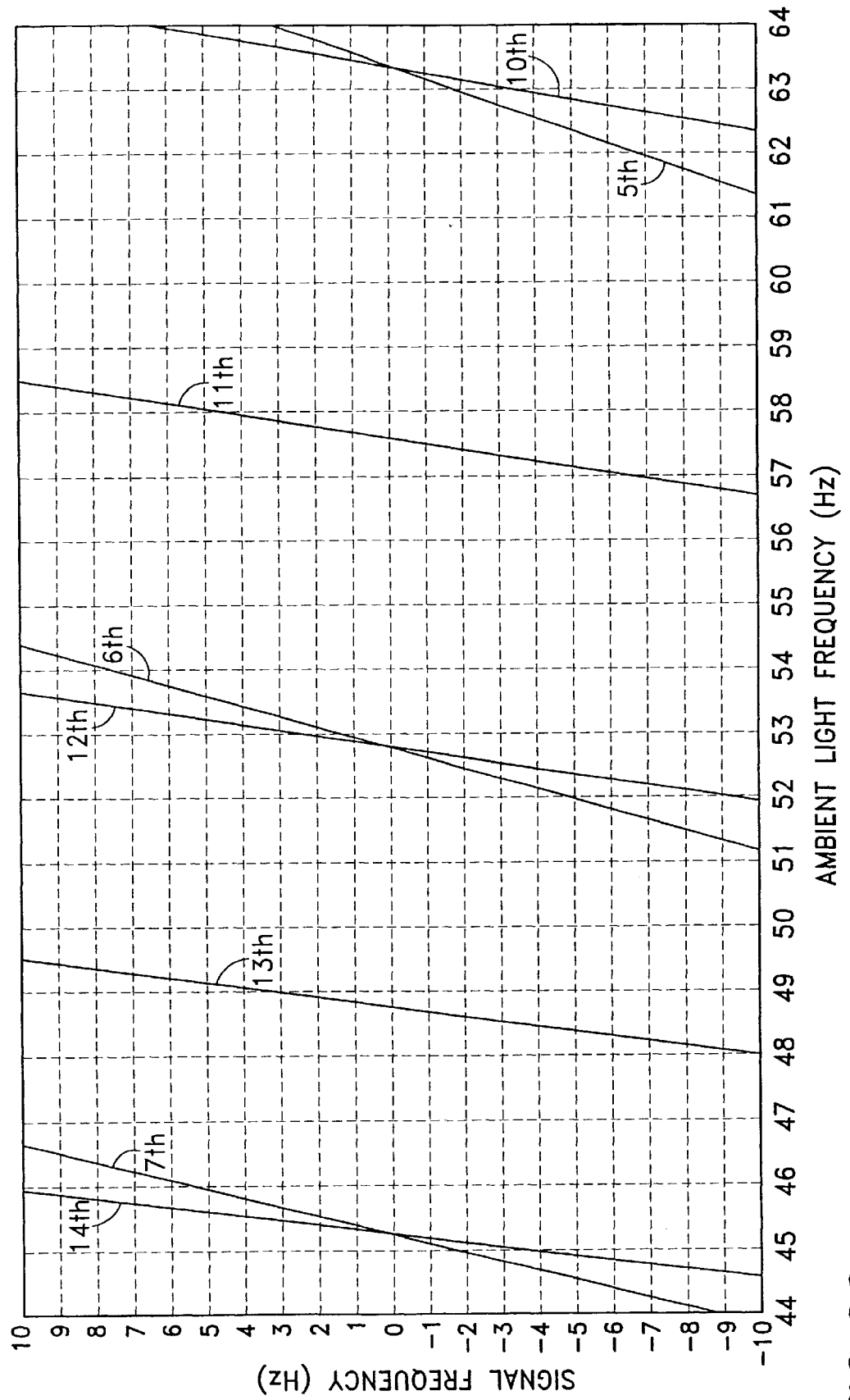
FIG. 20 is a graph to be used in connection with graphical method for designing a demodulation system to minimize interference due to ambient light.

The process leading to Equation 57 is illustrated graphically by FIG. 20, where the harmonics of the ambient light frequency $f_a$ (in Hz) are plotted versus the plethysmograph signal frequency (also in Hz). FIG. 20 has an x-axis showing the ambient light frequency from 44 Hz to 64 Hz. The ambient light frequency will usually correspond to the frequency of the power lines, which is nominally 60 Hz (in the U.S.) and 50 Hz (outside the U.S.). However, power line frequency regulation typically varies somewhat, and thus FIG. 20 shows frequencies above and below the nominal frequencies.

FIG. 20 also shows a y-axis showing the plethysmograph signal frequency from -10 Hz to 10 Hz. One skilled in the art will recognize that negative frequencies occur in the mathematics described above. In particular, a signal that is modulated from baseband up to some carrier frequency will exhibit two sidebands, a sideband above the carrier frequency corresponding to the frequency of the baseband signal, and a sideband below the carrier frequency corresponding to the negative of the baseband frequency. Thus, when dealing with modulation and demodulation, it is convenient to deal with positive and negative frequencies.

FIG. 20 also shows harmonic lines corresponding to the 5$^{th}$, 6$^{th}$, 7$^{th}$, 10$^{th}$, 11$^{th}$, 12$^{th}$, 13$^{th}$, and 14$^{th}$ harmonics of the ambient light frequency. The harmonic lines correspond to the harmonics produced in the plethysmograph signal by the demodulation (mixing down) of harmonics of the power line frequency. The lines in FIG. 20 are calculated using Equation 54 for 1/T=316.72 Hz. Some of the harmonic lines correspond to y($f_a$,n) and some correspond to z($f_a$,n) from Equation 54. Harmonic lines that are not shown (e.g., the line corresponding to the 8$^{th}$ harmonic) fall outside the displayed limits of the x-axis and y-axis.

FIG. 20 can be used to determine the stop band frequencies as shown in Equation 56. For example, the harmonic lines in FIG. 20 show that for an ambient light frequency of 49 Hz, the 13$^{th}$ harmonic of the ambient light frequency will appear in the plethysmograph signal at approximately 3 Hz. Thus, FIG. 20 shows that for plethysmograph bandwidth of 10 Hz, none of the first 14 harmonics of the ambient light will appear in the plethysmograph signal for ambient light frequencies between approximately 61.2 Hz and approximately 58.5 Hz, which is consistent with Equation 57. The first ambient harmonics that do appear for a plethysmograph bandwidth of 10 Hz are the 5$^{th}$ harmonic and the 11$^{th}$ harmonic.

Other Embodiments

In the preferred embodiment of the present invention, the hardware described above is implemented in a digital signal processor and associated circuitry. The LED modulation block 104 and the LED demodulation state table block 352 comprise algorithms implemented by program code executed by the digital signal processor. In addition, the configuration variables, such as for example, the hardware delay value, the hardware distortion value and the hardware scale value are provided as inputs to the digital signal processor when it is set up. For example, the main operating program of the digital signal processor may be stored in non-volatile ROM or PROM, and the variables may be stored in flash memory during a setup procedure. Techniques for communicating to and from a digital signal processor during such setup procedures are well known to persons of skill in the art, and will not be described in detail herein. For example, the configuration bus 310, discussed above, represents a communication path to the flash memory during such a setup procedure. The data provided to the configuration bus 310 may be provided by a system operator (not shown) or the data may be provided from look-up tables (not shown) maintained for different embodiments of the LEDs 106, 108 and the detector 150.

Although described above in connection with a pulse oximetry system wherein a parameter to be measured is the attenuation of red and infrared light passing through a portion of a subject's body, it should be understood that the method and apparatus described herein can also be used for other measurements where two or more signals are passed through a system to be analyzed. In particular, the present invention can be used to demodulate two combined parametric signals responsive to the system to be analyzed where the two parametric signals have a predetermined timing relationship between them, as described herein.

One skilled in the art will recognize that the lowpass filters provided in connection with the decimation blocks may provide other filter functions in addition to lowpass filtering. Thus, for example, the lowpass filters 1620, 1622, 1630, 1640, 1650, 1720, 1730, and 1740, and the decimators 1820, 1830, 1834, and 1840 may provide other filter functions (in addition to lowpass filtering) such as, for example, bandpass filtering, bandstop filtering, etc. Moreover, the post-demodulation decimation rate $R_2$ need not be the same for each output channel. Thus, for example, in FIG. 18, the decimator 1840 may have a first decimation rate $R_2=r_1$ while the decimators 1830 and 1834 have a second decimation rate $R_2=r_2$.

Although described above in connection with a particular embodiment of the present invention, it should be understood the description of the embodiment is illustrative of the invention and are not intended to be limiting. Various modifications and applications may occur to those skilled in the art without departing from the true spirit and scope of the invention as defined in the appended claims.

What is claimed is:

1. A method of minimizing crosstalk between two signals generated by applying a first pulse and a second pulse to measure a parameter, wherein said first pulse and said second pulse are applied periodically at a first repetition rate defining a period, and wherein said first pulse is generated during a first interval in each period and said second pulse is generated during a second interval in each period, said second interval spaced apart from said first interval, said first and second pulses producing first and second parametric signals responsive to said parameter, said first and second parametric signals being received by a single detector which outputs a composite signal responsive to said first and second parametric signals, said method comprising the steps of:

providing said composite signal to an analog to digital converter to produce a sequence of digital values;

decimating said sequence of digital values to produce a decimated sequence of digital values according to a decimation rate that produces relatively little shaping of said first and second parametric signals and that produces a relatively larger shaping of a noise component of said composite signal according to a decimation rate that produces relatively little shaping of said first and second parametric signals and that produces a relatively larger shaping of a noise component of said composite signal, said decimation rate adjusted according to noise in said first or second parametric signals;

applying a first sequence of demodulation coefficients to said decimated sequence of digital values to generate a first demodulated output signal;

applying a second sequence of demodulation coefficients to said decimated sequence of digital values to generate a second demodulated output signal;

lowpass filtering said first demodulated output signal to generate a first recovered output signal responsive to said first parametric signal; and lowpass filtering said second demodulated output signal to generate a second recovered output signal responsive to said second parametric signal.

2. A method of minimizing crosstalk between two signals generated by applying a first pulse and a second pulse to measure a parameter, wherein said first pulse and said second pulse are applied periodically at a first repetition rate defining a period, and wherein said first pulse is generated during a first interval in each period and said second pulse is generated during a second interval in each period, said second interval spaced apart from said first interval, said first and second pulses producing first and second parametric signals responsive to said parameter, said first and second parametric signals being received by a single detector which outputs a composite signal responsive to said first and second parametric signals, said method comprising the steps of:

providing said composite signal to an analog to digital converter to produce a sequence of digital values;

decimating said sequence of digital values to produce a decimated sequence of digital values;

applying a first sequence of demodulation coefficients to said decimated sequence of digital values to generate a first demodulated output signal;

applying a second sequence of demodulation coefficients to said decimated sequence of digital values to generate a second demodulated output signal;

lowpass filtering said first demodulated output signal to generate a first recovered output signal responsive to said first parametric signal;

lowpass filtering said second demodulated output signal to generate a second recovered output signal responsive to said second parametric signal applying a third sequence of demodulation coefficients to said decimated sequence of digital values to generate a third demodulated output signal; and lowpass filtering said third demodulated output signal to generate a recovered output signal responsive to noise detected by said detector.

3. A pulse oximetry system, comprising:

a modulation signal generator, said modulation signal generator generating a first modulation signal comprising a first pulse which repeats at a first repetition frequency, said first pulse having a duty cycle of less than 50%, said modulation signal generator generating a second modulation signal comprising a second pulse which also repeats at said first repetition frequency, said second pulse having said duty cycle of less than 50%, said second pulse occurring at non-overlapping times with respect to said first pulse;

a first transmitter which emits electromagnetic energy at a first wavelength in response to said first pulse;

a second transmitter which emits electromagnetic energy at a second wavelength in response to said second pulse;

a detector which receives electromagnetic energy at said first and second wavelengths after passing through a portion of a subject and which generates a detector output signal responsive to the received electromagnetic energy, said detector output signal including a signal component responsive to attenuation of said electromagnetic energy at said first wavelength and a signal component responsive to attenuation of said electromagnetic energy at said second wavelength;

a sampling analog to digital converter which converts said detector output into a sequence of digital values;

a decimator which decimates said sequence of digital values at a first decimation rate to produce a decimated sequence;

a first demodulator which multiplies said decimated sequence by a demodulation sequence and generates a first demodulated output signal; and a processor that selects said first decimation rate to improve said first demodulated output signal;

a second demodulator which multiplies said decimated sequence by a second demodulation sequence and generates a second demodulated output signal.

4. The apparatus of claim 3 further comprising a third demodulator which multiplies said decimated sequence by a third demodulation sequence and generates a third demodulated output signal corresponding to noise produced by said detector.

5. The apparatus of claim 4, wherein said processor selects said first decimation rate by examining said third demodulated output signal.

6. The apparatus of claim 3 wherein said decimator has a decimation rate equal to the number of said samples produced during said duty cycle.

7. The apparatus of claim 3, wherein said first demodulator decimates said first demodulated output signal according to a second decimation rate.

8. The apparatus of claim 3, wherein said first demodulator decimates said first demodulated output signal according to a second decimation rate, and wherein said processor selects said second decimation rate.

9. The apparatus of claim 3, wherein said first decimation rate produces relatively little shaping of signal components corresponding to a first desired signal component, and wherein said first decimation rate produces relatively more shaping of signal components corresponding to noise.

* * * * *